(12) United States Patent
Nagae et al.

(10) Patent No.: US 10,088,560 B2
(45) Date of Patent: Oct. 2, 2018

(54) OBJECT INFORMATION ACQUIRING APPARATUS AND OBJECT INFORMATION ACQUIRING METHOD

(75) Inventors: Kenichi Nagae, Yokohama (JP); Toru Sato, Kyoto (JP)

(73) Assignee: CANON KABUSHIKI KAISHA, Tokyo (JP)

(*) Notice: Subject to any disclaimer, the term of this patent is extended or adjusted under 35 U.S.C. 154(b) by 487 days.

(21) Appl. No.: 14/114,322

(22) PCT Filed: Apr. 26, 2012

(86) PCT No.: PCT/JP2012/002876
§ 371 (c)(1),
(2), (4) Date: Oct. 28, 2013

(87) PCT Pub. No.: WO2012/153480
PCT Pub. Date: Nov. 15, 2012

(65) Prior Publication Data
US 2014/0056105 A1 Feb. 27, 2014

(30) Foreign Application Priority Data
May 10, 2011 (JP) ................................. 2011-105318

(51) Int. Cl.
*G01S 7/52* (2006.01)
*G01N 21/17* (2006.01)

(52) U.S. Cl.
CPC ...... *G01S 7/52017* (2013.01); *G01N 21/1702* (2013.01); *G01S 7/52047* (2013.01)

(58) Field of Classification Search
CPC ............ G01S 7/52017; G01S 7/52047; G01N 21/1702
(Continued)

(56) References Cited

U.S. PATENT DOCUMENTS

2004/0193052 A1* 9/2004 Ogawa ............... G01S 7/52047
600/440
2008/0114241 A1* 5/2008 Randall ............... A61B 5/0002
600/443
(Continued)

FOREIGN PATENT DOCUMENTS

JP 2010-183979 8/2010
WO WO 2010/100868 9/2010
(Continued)

OTHER PUBLICATIONS

Office Action issued Apr. 7, 2015 in counterpart Japanese patent application 2011-105318, with translation.
(Continued)

*Primary Examiner* — James R Hulka
(74) *Attorney, Agent, or Firm* — Fitzpatrick, Cella, Harper & Scinto

(57) ABSTRACT

The present invention employs an object information acquiring apparatus comprising a plurality of conversion elements which receive acoustic waves emitted from an object and convert the acoustic waves into electrical signals, a correlation calculator which calculates correlation data by using the plurality of electrical signals output from the plurality of conversion elements, an average correlation calculator which calculates an average correlation matrix by extracting a plurality of submatrices from the correlation data and averaging the submatrices, and an adaptive signal processor which generates power distribution by performing adaptive signal processing by using the average correlation matrix and calculating the power of each target position, wherein the correlation calculator calculates the correlation data by obtaining the correlation of input signals that are separated by at least one input signal among the input signals.

38 Claims, 18 Drawing Sheets

(58) Field of Classification Search
USPC .......................................................... 367/87
See application file for complete search history.

(56) References Cited

U.S. PATENT DOCUMENTS

| | | | |
|---|---|---|---|
| 2011/0307181 A1* | 12/2011 | Nagae ................. | G01S 7/52047 |
| | | | 702/19 |
| 2012/0022373 A1* | 1/2012 | Tateyama ............ | G01S 7/52034 |
| | | | 600/437 |
| 2012/0044785 A1 | 2/2012 | Yoda et al. ...................... | 367/92 |
| 2012/0314534 A1 | 12/2012 | Yoda et al. ........................ | 367/7 |
| 2013/0338944 A1 | 12/2013 | Nagae et al. .................... | 702/56 |
| 2014/0051970 A1 | 2/2014 | Ebisawa et al. ............... | 600/407 |
| 2014/0206998 A1 | 7/2014 | Taki et al. ..................... | 600/443 |

FOREIGN PATENT DOCUMENTS

| | | | | |
|---|---|---|---|---|
| WO | WO2010100868 | * | 9/2010 | ............... G10S 7/52 |
| WO | WO 2010/137453 | | 12/2010 | |
| WO | WO2010137453 | * | 12/2010 | ............... G10S 7/52 |

OTHER PUBLICATIONS

M. Sasso et al., "Medical Ultrasound Imaging Using the Fully Adaptive Beamformer", Proc. Acoustics, *2005 IEEE Conference on Acoustics, Speech and Signal Processing*, pp. 489-492 (2005).
S. Park et al., "Adaptive Beamforming for Photoacoustic Imaging", *Optics Letters*, Vo. 33, No. 12, pp. 1291-1293 (Jun. 15, 2008).

* cited by examiner

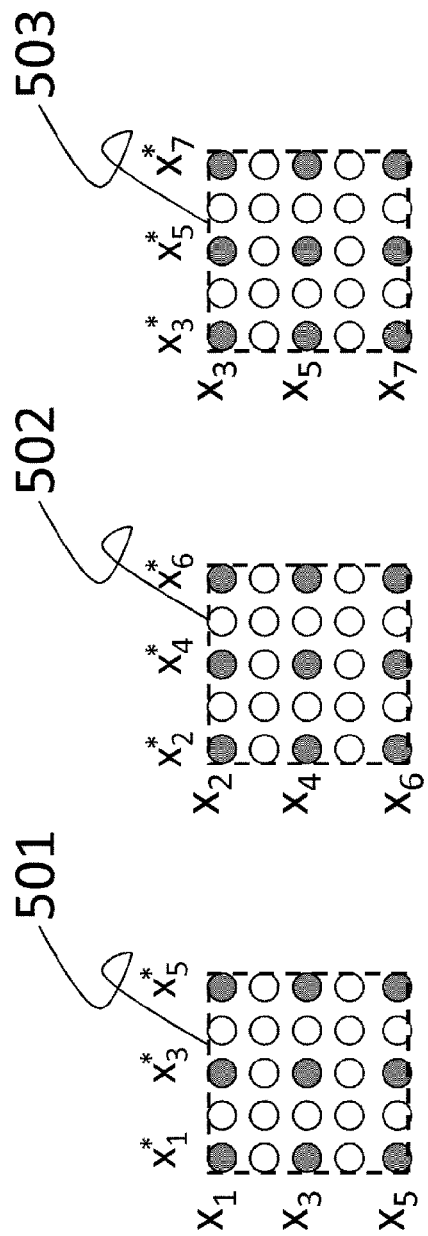
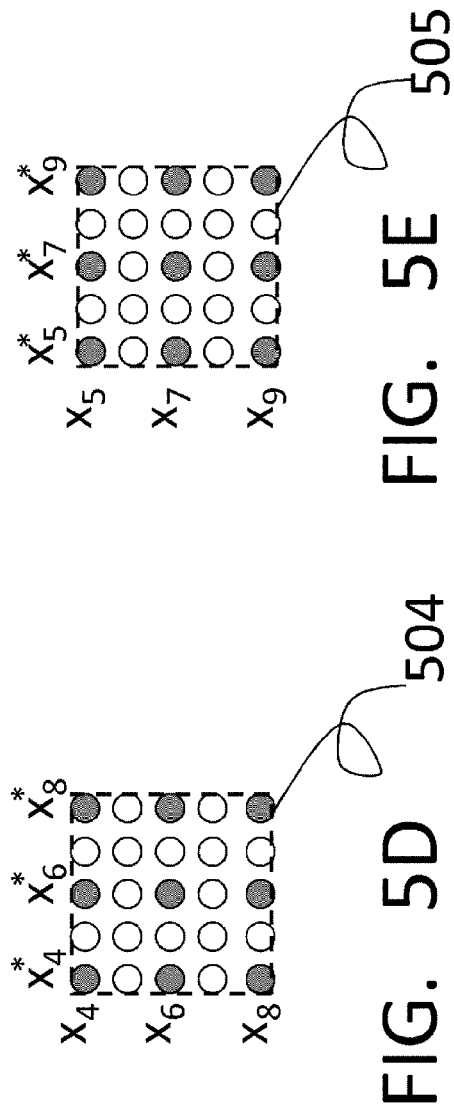
FIG. 5A  FIG. 5B  FIG. 5C  FIG. 5D  FIG. 5E

OBJECT INFORMATION ACQUIRING APPARATUS AND OBJECT INFORMATION ACQUIRING METHOD

TECHNICAL FIELD

The present invention relates to an object information acquiring apparatus and an object information acquiring method for performing adaptive signal processing.

BACKGROUND ART

There is an apparatus which acquires a cross-sectional image or a three-dimensional image of the inside of an object by receiving ultrasound waves from within the object. As an example of such an apparatus, there is a type which uses ultrasound waves for both transmission and reception; for instance, a type which transmits ultrasound waves and receives the reflected waves thereof. As a different example, there is a type which utilizes the photoacoustic effect in which the object that absorbed light energy is subject to adiabatic expansion and generates elastic waves (ultrasound waves) and transmits light energy into the object and receives the generated ultrasound waves; for instance, a type which uses light for transmission and uses ultrasound waves for reception.

Meanwhile, there is adaptive signal processing that has been developed in the field of radars. Adaptive signal processing is a processing method of adaptively changing the amplitude or phase of the respective signals according to the signals that were received at a plurality of receiving positions. For example, there is Constrained Minimization of Power (CMP) as one type of adaptive signal processing. This is a method where, upon receiving signals with a plurality of elements, processing is performed so as to minimize the signal power in a state of fixing the sensitivity related to a certain direction. With adaptive signal processing, the processing parameter of the received signal is adaptively changed for each such received signal. This kind of adaptive signal processing has the effect of improving the spatial resolution, in particular the resolution of the orientation direction.

Non Patent Literature 1 describes the results of improving the resolution by combining the foregoing adaptive signal processing with ultrasound waves, and Non Patent Literature 2 describes the results of imaging by combining the adaptive signal processing with photoacoustics.

As described in Non Patent Literatures 1 and 2, the spatial averaging method is used in order to inhibit the influence of interference waves having high correlation upon applying the CMP method to ultrasound received signals. Here, the spatial averaging method is a method of implementing adaptive processing by obtaining a correlation matrix from the received signals, and thereafter extracting a correlation submatrix obtained by extracting and averaging the submatrices.

Here, the processing upon applying adaptive signal processing to the received signals of the ultrasound waves is explained taking CMP as an example, and the necessity of using the spatial averaging method is thereafter explained.

Foremost, the process up to calculating the correlation matrix from the received signals is explained. Hilbert transformation is performed to the signals received by a plurality of elements and the received signals are subject to complex representation. Here, the s-th sample of the signals obtained by processing the received signals from the k-th element is set as $x_k[s]$, and the input vector $X[s]$ of the s-th sample is defined as shown in Formula (1) below. Note that, here, M represents the total number of conversion elements. Moreover, T represents a transposed matrix.

[Math. 1]

$$X[s]=[x_1[s],x_2[s],\ldots,x_M[s]]^T \qquad (1)$$

This input vector $X[s]$ is used to calculate the correlation matrix $R_{xx}$ as shown in Formula (2).

[Math. 2]

$$\begin{aligned}R_{xx} &= E[X[s]X^H[s]] \\ &= \begin{pmatrix} E[x_1[s]x_1^*[s]] & E[x_1[s]x_2^*[s]] & \ldots & E[x_1[s]x_M^*[s]] \\ E[x_2[s]x_1^*[s]] & E[x_2[s]x_2^*[s]] & \ldots & E[x_2[s]x_M^*[s]] \\ \vdots & \vdots & \ddots & \vdots \\ E[x_M[s]x_1^*[s]] & E[x_M[s]x_2^*[s]] & \ldots & E[x_M[s]x_M^*[s]] \end{pmatrix}\end{aligned} \qquad (2)$$

The superscript H in the formula represents the complex conjugate transpose, and the superscript * represents the complex conjugate. E[ ] is the processing of calculating the time average, and represents that the average is calculated by changing the number (s in this example) of samples. The correlation matrix is obtained as described above.

Subsequently, the weight vector W based on the conditions of Formula (3) below is obtained.

[Math. 3]

$$\left.\begin{aligned}\min_{W}\,(W^H R_{xx} W) \\ \text{subject to } W^H a = 1\end{aligned}\right\} \qquad (3)$$

These conditions represent that the output power ($W^H R_{xx} W$) is minimized in a state where the sensitivity ($W^H a$) in the intended direction is constrained to 1. Note that "a" is the steering vector, and defines the intended direction; that is, the observation direction.

The optimal weight Wopt is calculated from the foregoing conditions as shown in Formula (4).

[Math. 4]

$$W_{opt} = \frac{R_{xx}^{-1} a}{a^H R_{xx}^{-1} a} \qquad (4)$$

As a result of using this optimal weight, the output power can be minimized in a state where the sensitivity of the intended direction is set to 1. The receiving arrays using this optimal weight form a receiving pattern in which the sensitivity of the intended direction, or the observation direction, is 1, and which has a directionality of low sensitivity relative to the arrival direction of the noise components.

Moreover, the power Pout from the intended direction can be represented as shown in Formula (5).

[Math. 5]

$$P_{out} = \frac{1}{2a^H R_{xx}^{-1} a} \qquad (5)$$

The basic principle of the CMP method is as described above.

In a general ultrasound imaging apparatus, a plurality of transmissions and receptions (typically 100 times or more) are performed upon generating one frame worth of a cross-sectional image while changing the transmitting/receiving direction or position. When acquiring a cross-sectional image or a three-dimensional image based on the transmission and reception of ultrasound waves as described above, the observation direction of the adaptive signal processing described above is generally caused to coincide with the transmitting direction of the ultrasound waves.

Meanwhile, although the foregoing principle is satisfied when the noise components and the intended waves have no correlativity, it is not satisfied when the noise components and the intended waves have correlativity. Specifically, when noise components having correlativity with the intended waves are received, formed is a receiving pattern of directionality having a sensitivity of 1 in the direction of the intended waves, but also an opposite phase sensitivity in the direction of the noise components. This is because, as a result of adding the noise components to the intended waves in an opposite phase in order to minimize the signals that are output, the output signals are caused to approach 0.

Meanwhile, when performing imaging by using the transmission/reception of ultrasound waves and the photoacoustic effect, the noise component is likely to have high correlativity with the intended component. For example, with imaging based on ultrasound waves, the reflected waves of the ultrasound waves that were transmitted on one's own are used in the imaging. Thus, the receives waves (i.e., noise components) that are reflected from directions other than the intended direction have high correlativity with the intended waves. Moreover, with imaging utilizing the photoacoustic effect also, the incident light spreads over a wide range due to the scattering effect, and the ultrasound waves generated from that wide range are likely to have high correlativity.

The spatial averaging method is the method of applying the CMP method even in cases where the correlativity of the intended components and noise components is high as described above. With the spatial averaging method, a plurality of submatrices are extracted from the foregoing correlation matrix, and the optimal weight is obtained by using the spatial average correlation matrix that is calculated based on the average of such submatrices.

The spatial average correlation matrix $R'_{xx}$ can be calculated with Formula (7) based on Formula (6) below relating to the correlation submatrix.

[Math. 6]

$$X_n(t) = [x_n(t), x_{n+1}(t), \ldots, x_{n+K-1}(t)]^T \quad (6)$$

$$R'_{xx} = \sum_{n=1}^{N} z_n E[X_n(t) X_n^H(t)] \quad (7)$$

Note that N is the number of submatrices to be extracted, and K is the size of the submatrices obtained based on M−N+1. Moreover, Zn is the weight coefficient upon averaging the submatrices, and, while this will be the simple average in the case of Zn=1/N, it is also possible to use the hamming window, the banning window, or the Dolph-Chebycheff window as the weighting function. $R''_{xx}$ represents the submatrices in the correlation matrix $R_{xx}$ moving on the diagonal components of $R_{xx}$ and is a matrix having a size of K by K at a position where the (n, n) component of $R_{xx}$ is the first diagonal component thereof. Zn is the coefficient upon adding the respective submatrices, and this is adjusted so that the sum of Zn becomes 1.

FIG. 1 is a diagram schematically representing the processing upon calculating the spatial average correlation matrix. The correlation matrix 001 of 9 by 9 is calculated based on the multiplication of the input signal vectors X (x1 to x9) and its complex conjugate vectors $X^H$ (x*1 to x*9). A plurality of correlation matrices associated with the lapse of the receiving time are averaged, and the processing for calculating the expectation of the correlation is performed. Subsequently, by extracting five submatrices 002 of 5 by 5 enclosed by the dotted line and obtaining the average thereof, a spatial average correlation matrix of 5 by 5 can be obtained.

As a result of using the spatial average correlation matrix calculated as described above, the foregoing optimal weight Wopt and the power Pout from the intended direction can be respectively calculated from Formula (8) and Formula (9) below.

[Math. 7]

$$Wopt = \frac{R'^{-1}_{xx} a}{a^H R'^{-1}_{xx} a} \quad (8)$$

$$Pout = \frac{1}{2 a^H R'^{-1}_{xx} a} \quad (9)$$

The steering vector a in the foregoing case is a vector configured from K number of elements.

In the spatial averaging method, known is a correlation suppression factor which shows the effect of suppressing the correlativity interference waves as shown in Formula (10).

[Math. 8]

$$\xi = \sum_{n=1}^{N} Zn \exp\left[j \frac{2\pi d}{\lambda}\left(n - \frac{N+1}{2}\right)(\sin\theta c - \sin\theta s)\right] \quad (10)$$

ξ is the correlation suppression factor to be obtained,
d is the distance between the adjacent elements,
λ is the wavelength of the received signals,
θs is the observing direction,
θc is the arrival direction of the correlativity interference waves.

This formula is the same as the directionality synthesis of the N element linear array.

When this correlation suppression factor is small, the influence of the correlativity interference wave can be considerably suppressed.

Accordingly, with the CMP method, the correlation matrix and additionally the spatial average correlation matrix are obtained from the received signals, and the inverse matrix thereof can be used to calculate the complex weight or the power upon using the complex weight.

Since the distance from the position of the conversion elements can be set forth and the target direction can be defined by the steering vector depending on which sample of the received signals is used, the target position (distance and direction) in the object can be defined by the foregoing processing. The complex weight and the power upon using the complex weight are the weight and power upon setting the sensitivity relative to the signals from the target position to 1, and suppressing the signals arriving from other positions. In other words, signals from the target position can be selectively extracted with the CMP method and, consequently, the spatial resolution can be improved.

Note that, rather than directly obtaining the inverse matrix, calculation can also be performed based on the QR decomposition and the back substitution processing relative to the spatial average correlation matrix.

As a result of calculating the optimal weight by using the foregoing spatial average correlation matrix, even when noise components having high correlativity with the intended waves are received, the correlativity of that noise can be suppressed. Thus, even in cases where ultrasound waves are used for transmission and reception or when performing imaging using the photoacoustic effect, the effect of improving the spatial resolution of the orientation direction based on the CMP method is yielded.

CITATION LIST

Non Patent Literature

[NPL 1]
Proc. Acoustics, Speech Signal Process, pp. 489-492 (March 2005)
[NPL 2]
OPTICS LETTERS, Vol. 33, No. 12, pp. 1291-1293 (Jun. 15, 2008)

SUMMARY OF INVENTION

Technical Problem

Nevertheless, when using the adaptive signal processing in order to obtain a higher spatial resolution, the processing volume thereof becomes a problem.

In adaptive signal processing, it is necessary to calculate the inverse matrix or calculate the QR decomposition or eigenvalue in relation to the matrix of a size corresponding to the number of input signals. It is known that the calculation volume of this kind of processing increases in proportion to the cube of the matrix size. For example, in the case of adaptive signal processing using a one-dimensional probe that receives signals with the apertures of 96 elements in the array direction, the correlation matrix will have a size of 96 by 96. In addition, upon applying the spatial averaging method, a spatial average correlation matrix of typically half the size; for instance, a size of 48 by 48 is obtained. In the adaptive signal processing, it is necessary to perform inverse matrix calculation or QR decomposition of the spatial average correlation matrix. In the actual measurement, to perform the operation of obtaining the inverse matrix of a 48 by 48 matrix relative to the ultrasound signals that are input continuously will incur an increase of the processing volume, and is not realistic.

The present invention was devised in view of the foregoing problems. Thus, an object of this invention is to provide technology that enables the acquisition of images having a high spatial resolution while suppressing the signal processing volume in an object information acquiring apparatus and an object information acquiring method for receiving ultrasound signals and performing adaptive signal processing.

Solution to Problem

The present invention provides an object information acquiring apparatus, comprising:

a plurality of conversion elements which receive acoustic waves emitted from an object and convert the acoustic waves into electrical signals;

a correlation calculator which calculates correlation data by using the plurality of electrical signals output from the plurality of conversion elements;

an average correlation calculator which calculates an average correlation matrix by extracting a plurality of submatrices from the correlation data and averaging the submatrices; and an adaptive signal processor which generates power distribution by performing adaptive signal processing by using the average correlation matrix and calculating the power of each target position, wherein the correlation calculator calculates the correlation data by obtaining the correlation of input signals that are separated by at least one input signal among the input signals input to the correlation calculator.

The present invention also provides an object information acquiring method, comprising:

a correlation calculation step of calculating correlation data by using a plurality of electrical signals output from a plurality of conversion elements which receive acoustic waves emitted from an object;

an average correlation calculation step of calculating an average correlation matrix by extracting a plurality of submatrices from the correlation data and averaging the submatrices; and an adaptive signal processing step of generating power distribution by performing adaptive signal processing by using the average correlation matrix and calculating the power of each target position, wherein, in the correlation calculation step, the correlation data is calculated by obtaining the correlation of input signals that are separated by at least one input signal among the input signals input in the correlation calculation step.

Advantageous Effects of Invention

According to the present invention, it is possible to provide technology that enables the acquisition of images having a high spatial resolution while suppressing the signal processing volume in an object information acquiring apparatus and an object information acquiring method for receiving ultrasound signals and performing adaptive signal processing.

Further features of the present invention will become apparent from the following description of exemplary embodiments with reference to the attached drawings.

BRIEF DESCRIPTION OF DRAWINGS

FIGS. 5A to 5E are diagrams schematically showing the processing of calculating the average correlation matrix.

DESCRIPTION OF EMBODIMENTS

The embodiments for implementing the present invention are now explained with reference to the appended drawings.

The ultrasound imaging apparatus includes an apparatus which transmits ultrasound waves to an object, and acquires the reflected ultrasound echoes. In addition, the ultrasound imaging apparatus of the present invention includes an apparatus which receives acoustic waves generated in the object by irradiating the object with light (electromagnetic waves), and uses the photoacoustic effect of acquiring object information as image data. Accordingly, the ultrasound imaging apparatus of the present invention can also be referred to as an object information acquiring apparatus. When the object is a biological object, the object information acquiring apparatus can also be referred to as a biological information acquiring apparatus. Here, acoustic waves are typically ultrasound waves, and include elastic waves referred to as sound waves, ultrasound waves, photoacoustic waves, and optical ultrasound waves.

With the former object information acquiring apparatus that uses the ultrasound echoes, object information is information which reflects the differences in the acoustic impedance of the tissues inside the object. With the latter object information acquiring apparatus that uses the photoacoustic effect, object information shows the generation source distribution of the acoustic waves generated by optical irradiation, the initial sound pressure distribution in the object, the light energy absorption coefficient density distribution that is derived from the initial sound pressure distribution, the absorption coefficient distribution, or the concentration distribution of the substance configuring the tissues. The substance concentration distribution is, for example, oxygen saturation distribution or oxidized/reduced hemoglobin concentration distribution. The power distribution that is generated and acquired in the present invention is the distribution corresponding to the foregoing object information, and this power distribution is acquired as the image data.

Figure 1:
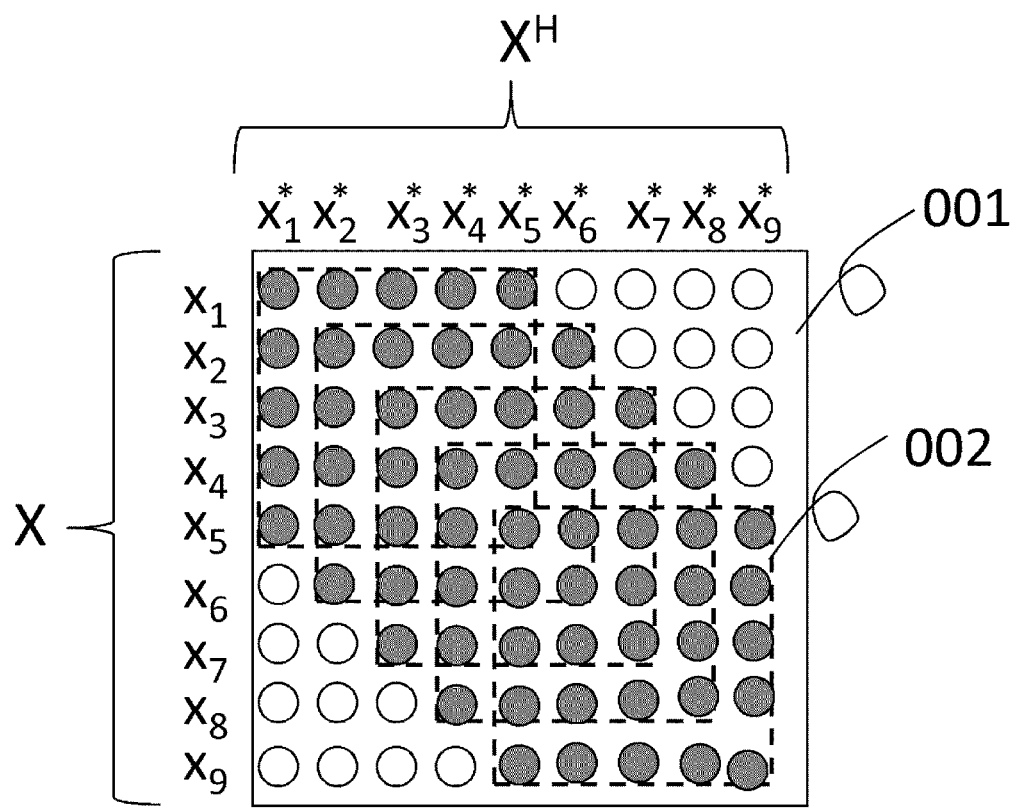
FIG. 1 is a diagram schematically showing the processing of calculating the spatial average correlation matrix.
Figure 2:
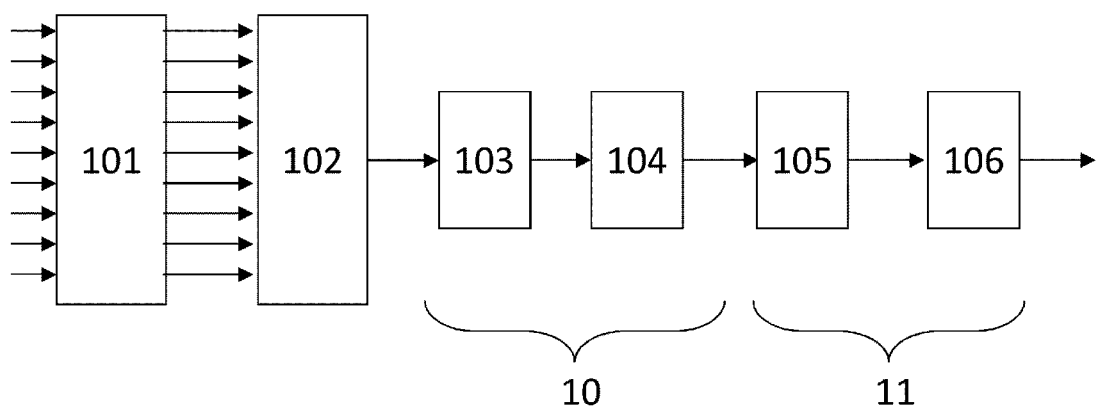
FIG. 2 is a diagram schematically showing the signal processing circuit in the present invention.
Figure 3:
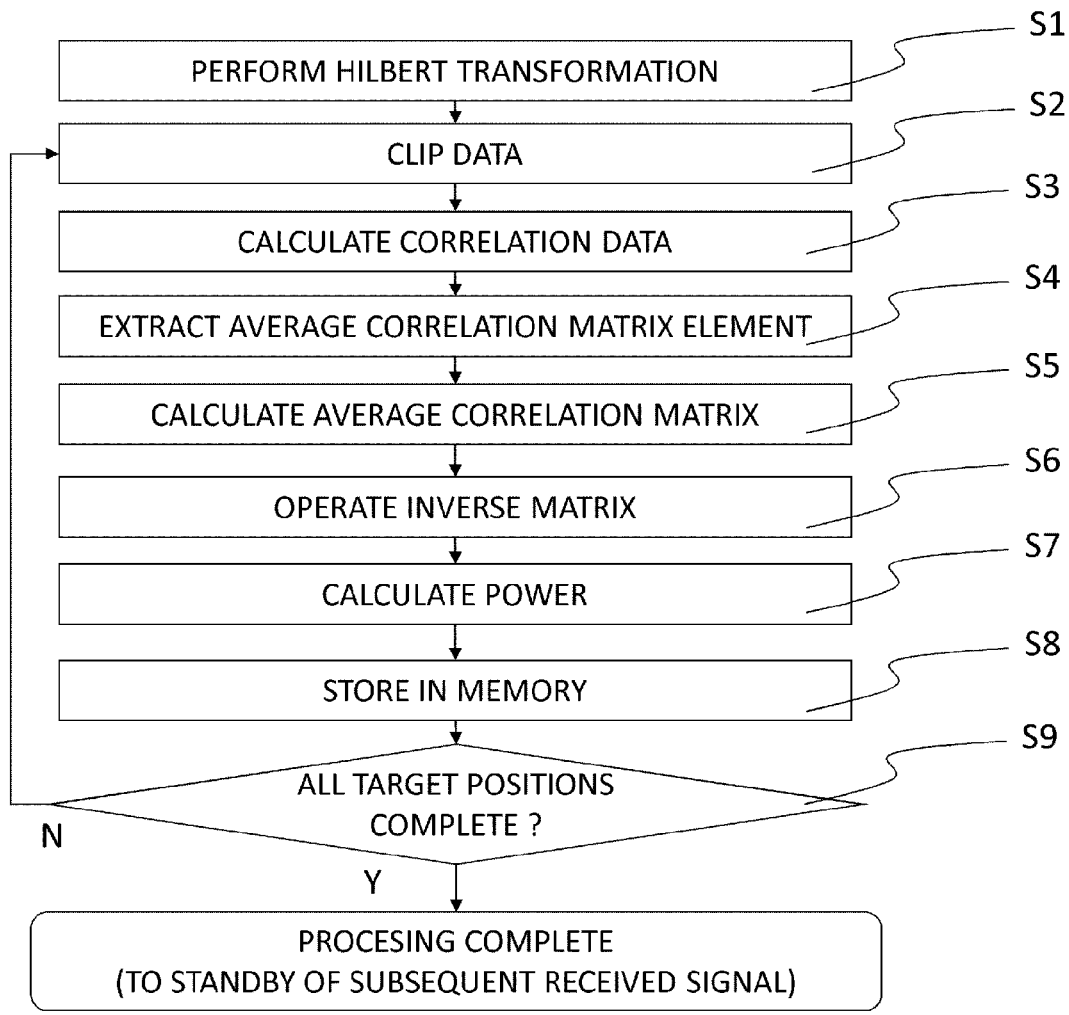
FIG. 3 is a diagram schematically showing the processing flow in the present invention.

The outline of the signal processing section of the present invention is now explained with reference to FIG. 2 to FIG. 6. FIG. 2 is a diagram schematically showing the signal processing circuit. FIG. 3 is a diagram schematically showing the processing flow, and the step number in the ensuing explanation refers to the number in the processing flow.

The signal processing circuit of FIG. 2 includes a Hilbert transformation circuit 101, a correlation calculation circuit 102, an element extraction circuit 103, an element average circuit 104, an inverse matrix operation circuit 105, and a power calculation circuit 106. The element extraction circuit 103 and the element average circuit 104 configure the average circuit 10. The inverse matrix operation circuit 105 and the power calculation circuit 106 configure the adaptive processing circuit 11. The correlation calculation circuit includes the correlation calculator and the average correlation calculator of the present invention. The adaptive signal processing circuit corresponds to the adaptive signal processor of the present invention.

A plurality of electrical signals output from a plurality of conversion elements not shown are AD-converted into digital data, and subsequently subject to the Hilbert transformation by the Hilbert transformation circuit 101 (step S1).

Among the plurality of digital signals that were converted into a complex representation by the Hilbert transformation, data is clipped only for the time required for the averaging in order to calculate the correlation data (step S2).

The clipped data is used to calculate the correlation data using the correlation calculation circuit 102 (step S3).

The calculation of the correlation data according to the present invention is now explained with reference to FIG. 4.

Here, for example, let it be assumed that 9 elements worth of digital signals subject to complex representation were input. The correlation matrix 001 of FIG. 4 is a result of obtaining the correlation of signals (x1 to x9, x*1 to x*9) indicated vertically and horizontally. While a 9 by 9 correlation matrix 001 can be created by using 9 elements worth of signals, the correlation calculation circuit of the present invention performs multiplication only on the elements at the positions that are colored in FIG. 4. The positions of these elements that are subject to multiplication are the positions of the diagonal components of the correlation matrix 001, and the positions that are separated at intervals of one or more columns from the positions of the diagonal components. Here, the diagonal elements represent the self-correlation of the input signals. Moreover, the elements of combinations such as x1 and x*3, and x2 and x*4 of positions that are separated by one or more columns from the position of the diagonal components represent the correlation of input signals that are separated by at least one input signal among the signals input to the correlation calculation circuit (among the input signals to the correlation calculation circuit).

In the present invention, this kind of operation is repeatedly performed in the amount of the clipped data. Ultimately, the result of averaging the foregoing data is referred to as the correlation data, and these calculation results are output as correlation data. In the foregoing case, the colored elements; that is, the 33 elements are output as the correlation data, and this is differentiated from the correlation matrix that is obtained by using all input signals.

The average circuit 10 includes an element extraction circuit 103, and an element average circuit 104. The element extraction circuit 103 extracts the elements used in the average correlation matrix with the calculated correlation data as the input (step S4).

The element average circuit 104 averages the extracted elements and calculates the average correlation matrix (step S5). Based on the foregoing operation, the average correlation matrix is output.

FIG. 5 is a diagram explaining the concept of the processing of calculating the average correlation matrix.

Figure 4:
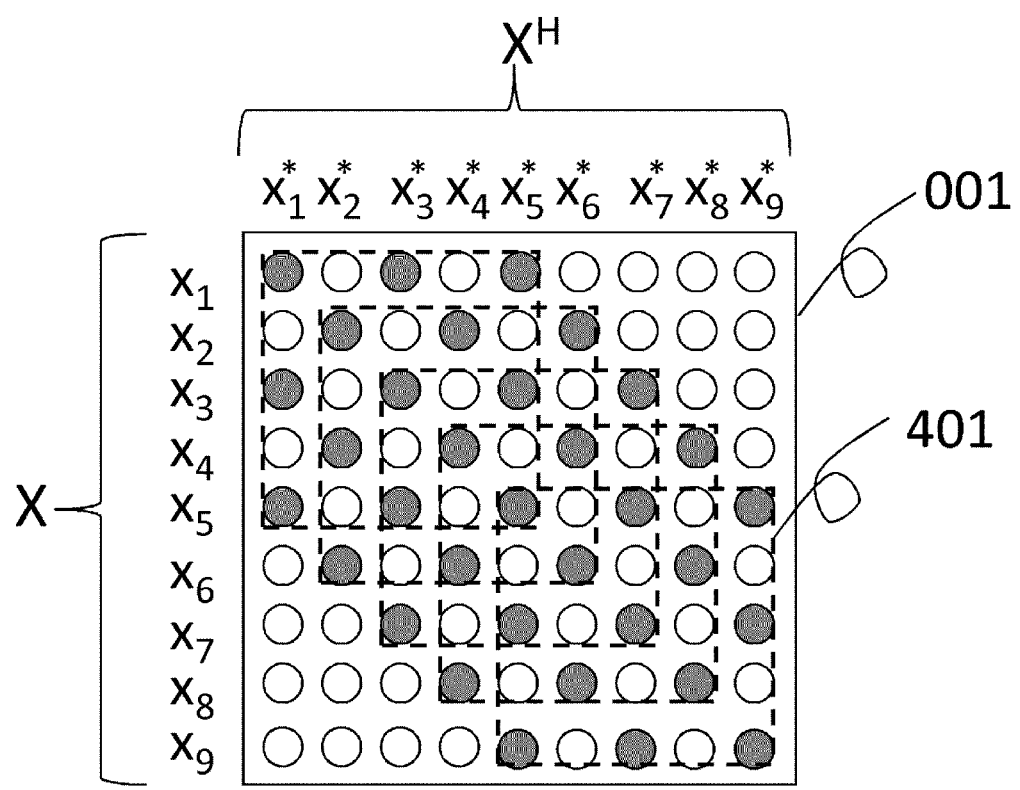
FIG. 4 is a diagram explaining the calculation method of correlation data based on the present invention.

Five submatrices 401 of FIG. 4 are formed. In FIG. 5, the five submatrices are shown as 501 to 505. FIGS. 5A to 5E respectively correspond to submatrices 501 to 505. The average correlation matrix is calculated by using the elements that are colored in the submatrices and averaging the respective submatrices. As described above, among the respective submatrices, it can be seen that the correlation of signals that are separated at least by one or more signals among the input signals is used.

As a result of performing this kind of processing, the ultimately obtained average correlation matrix will be a size of 3 by 3.

In the present invention, the matrix calculated as described above is referred to as an average correlation matrix, and this is differentiated from the spatial average correlation matrix that uses the results obtained by calculating all elements within the submatrix.

The adaptive processing circuit 11 includes an inverse matrix operation circuit 105, and a power calculation circuit 106. The inverse matrix operation circuit 105 operates the inverse matrix with the average correlation matrix $R'_{xx}$ as the input (step S6).

The power calculation circuit 106 calculates the power by using the operated inverse matrix (step S7). This calculation is performed according to Formula (11) below. Based on the foregoing operations, the power Pout that was calculated by using the adaptive signal processing is output. Note that "a" is the steering vector.

[Math. 9]

$$Pout = \frac{1}{2a^H R'^{-1}_{xx} a} \quad (11)$$

When considering a case where 9 elements worth of digital signals are input, the inverse matrix operation circuit will obtain the inverse matrix of a matrix having a size of 3 by 3. For example, if a 5 by 5 spatial average correlation matrix is input without using the present invention, a processing volume of approximately 4.6 times ($=(5/3)^3$) is required in comparison to the case of using the present invention.

Figure 6:
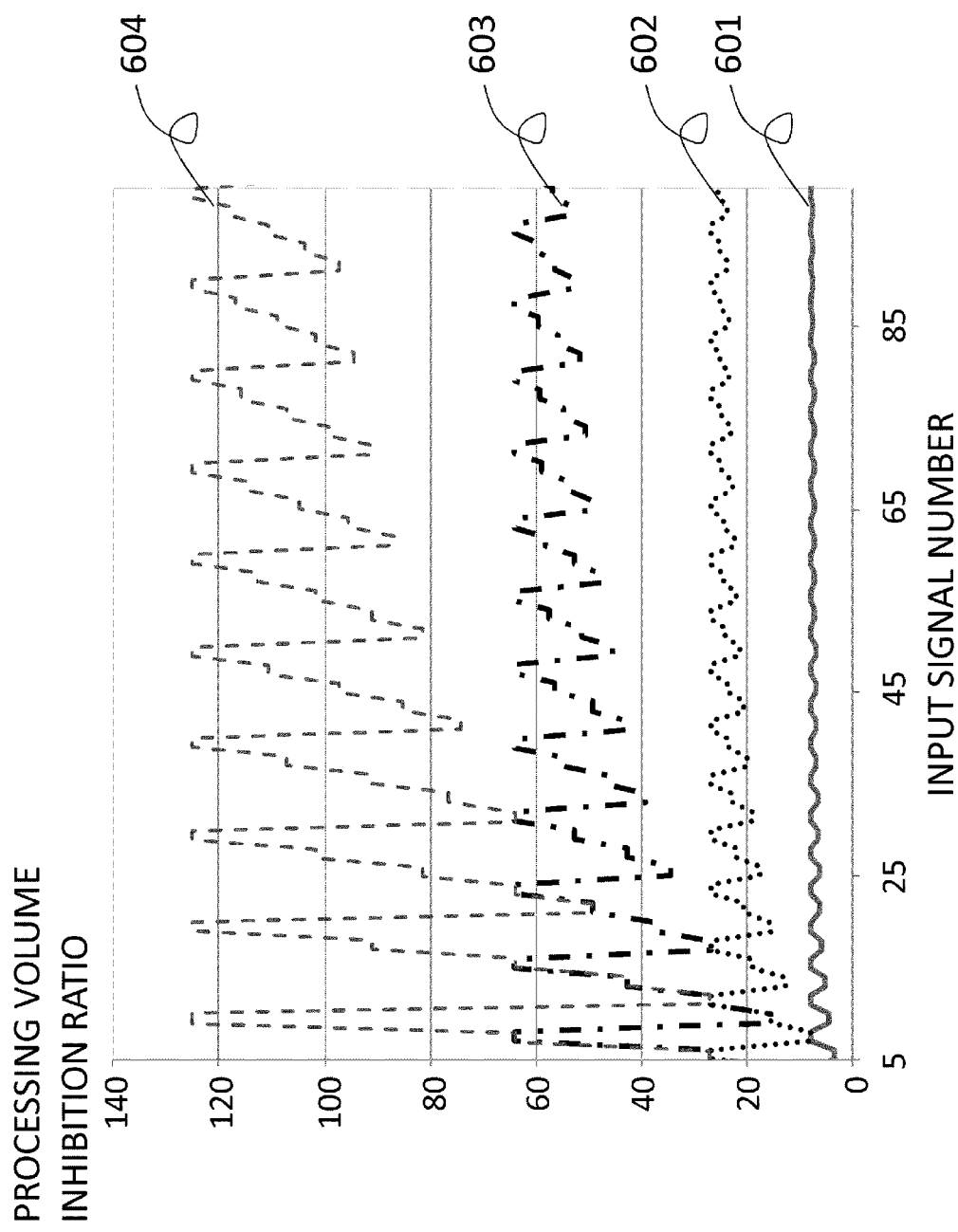
FIG. 6 is a diagram indicating the suppression ratio of the processing volume required for the inverse matrix operation.

FIG. 6 is a graph which plots the horizontal axis as the number of digital signals that are input, and the vertical axis as the suppression ratio of the processing volume that is required for the inverse matrix operation in the case of using the present invention and in the case of not using the present invention. Note that, in this graph, the size of the submatrices is set so that the size of the spatial average correlation matrix in the case of not using the present invention becomes half the number of input signals. Moreover, the size of the average correlation matrix of the present invention is set so that number of submatrices to be averaged becomes equal.

In the graph of FIG. 6, the plot 601 shows the suppression ratio of the processing volume in the case of using signals that are separated by one signal. The plot 602 shows the case of using signals that are separated by two signals. The plot 603 shows the case of using signals that are separated by three signals. The plot 604 shows the case of using signals that are separated by four signals. The suppression ratio is the ratio showing the percentile change of the processing volume that is required for obtaining the inverse matrix in the case of using the present invention.

For example, attention is given to the plot 603 representing the suppression ratio in the case of using signals that are separated by three signals. When the input is 16 CH, in the processing that does not use the present invention, nine submatrices having a size of 8 by 8 are extracted, and these submatrices are averaged to create a spatial average correlation matrix having a size of 8 by 8. Since the average correlation matrix based on the present invention uses signals that are separated by three signals, nine submatrices having a size of 2 by 2 are extracted, and an average correlation matrix having a size of 2 by 2 is ultimately created. In other words, under the foregoing circumstances, the suppression ratio of the processing volume based on the present invention is double ($64=(8/2)^3$).

Note that, here, nine submatrices were used to calculate the average correlation matrix. Nevertheless, the number of submatrices was limited to nine so that the processing that does not use the present invention and the number of submatrices will be equal, and in reality up to twelve submatrices can be extracted. As a result of increasing the number of submatrices as described above, the effect of suppressing the influence of the correlativity interference waves is yielded.

Moreover, when the input is 17 CH, the result will be a spatial average correlation matrix having a size of 9 by 9 (nine submatrices are extracted) and an average correlation matrix having a size of 3 by 3 (nine submatrices are extracted), and the suppression ratio of the processing volume is 27 times ($=(9/3)^3$).

Accordingly, the suppression ratio of the processing volume will increase or decrease depending on the size of the average correlation matrix relative to the number of input CHs or the signals used being separated by how many signals, but in all cases the processing volume can be reduced. In addition, when the number of input CHs is increased, the amplitude of the increase/decrease of the suppression ratio will decrease, and a high suppression ratio can be stably obtained.

When applying the present invention and performing adaptive signal processing by using the correlation of signals that are separated at least by one signal among the input signals, the processing volume of the inverse matrix operation can be reduced. Accordingly, the present invention can yield the effect of reducing the processing volume regardless of the number of digital signals that are input.

The power that is calculated by the adaptive processing circuit is stored in a memory (step S8).

In addition, the signal processing circuit determines whether the processing of all target positions that were set is complete (step S9).

When the processing of all target positions that were set is complete (S9=Y), the processing is ended and the process waits for the input of the subsequent received signal. When the processing of all target positions that were set is not complete (S9=N), the subsequent data is clipped and the same processing is repeated once again. The power obtained by the foregoing processing is arranged for each target position to generate the power distribution, and this is output to the display processing system. The display processing system performs log compression and image processing (edge enhancement, smoothing and the like) based on various image filters or the like, and displays the image data on an image display device.

Note that, here, the upper and lower elements sandwiching the diagonal elements in the correlation matrix were calculated, but since the correlation matrix is a Hermitian matrix, the processing can be performed by calculating either the diagonal elements or the elements in the upper or lower triangular matrix.

Moreover, although the inverse matrix was obtained in the foregoing case, the same results can also be obtained by performing QR decomposition to the average correlation matrix, and thereafter performing back substitution processing.

As described above, according to the present invention, it is possible to provide an apparatus capable of reducing the processing volume of adaptive signal processing and acquiring images having a high spatial resolution.

Here, explanation was provided by taking the CMP method as an example, but as a result of using the present invention, it is possible to reduce the size of the matrix that is input in the inverse matrix operation or the eigenvalue expansion having a large processing volume. Accordingly, without limitation to the CMP method that uses the inverse matrix operation, similar effects can also be obtained in other adaptive signal processing (for example, MUSIC method or ESPRIT method) that requires the eigenvalue expansion.

Attention is now given to the correlation suppression factor based on the present invention. The smaller the correlation suppression factor, the greater the effect of suppressing the influence of the correlativity interference waves. As described above, the correlation suppression factor is the same as the directionality synthesis of the N element linear array. The N element linear array is virtually formed by moving the extraction positions upon extracting the plurality of submatrices.

Figure 18:
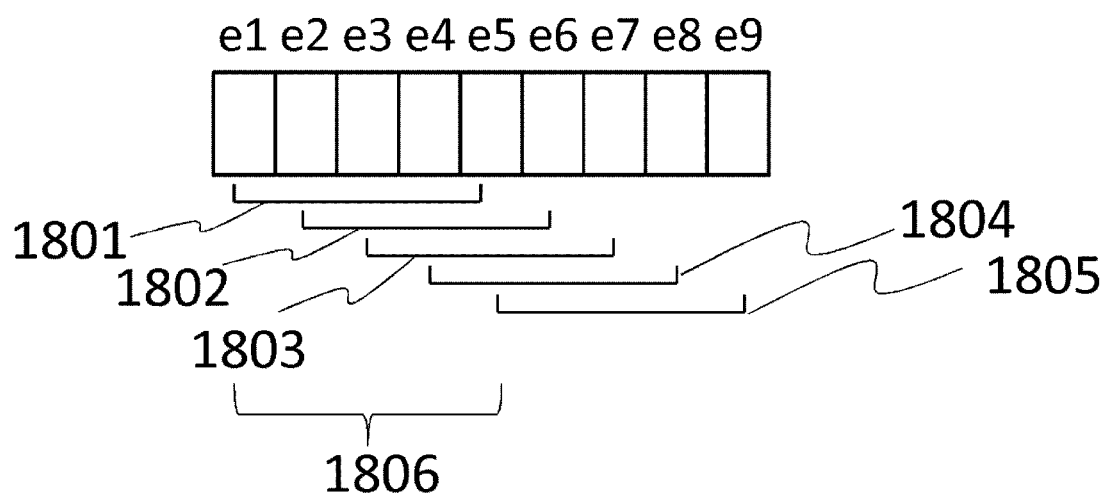
FIG. 18 is a diagram schematically showing the elements used in the spatial averaging method.

FIG. 18 is a diagram schematically representing the 9 conversion elements (e1 to e9). The signals received by the respective elements correspond from x1 to x9. The submatrix 501 shown in FIG. 5 is calculated from the signal received by the conversion element group 1801 shown as the conversion elements e1 to e5 in FIG. 18, and the submatrix 502 corresponds to the conversion element group 1802. Meanwhile, the elements of 1 row and 1 column of the average correlation matrix (having a size of 3 by 3) that is calculated from the submatrices shown in FIG. 5 is calculated by averaging the correlation of x1 and x*1, x2 and x*2, x3 and x*3, x4 and x*4, and x5 and x*5. These element groups that are averaged are elements that are continuous in the diagonal direction in the correlation matrix 001. Being continuous in the diagonal direction in the correlation matrix corresponds to the movement from the conversion element group 1801 to the conversion element group 1805 in FIG. 18, and the N element linear array that is virtually formed has the apertures shown in the range of 1805.

The present invention reduces the processing volume by using the correlation of signals separated at least by one signal among the input signals, but the extraction of the submatrices is performed at continuous positions in the correlation matrix 001. Thus, the correlation suppression factor of the average correlation matrix based on the present invention can suppress the influence caused by the correlativity interference waves in the same manner as the spatial average correlation matrix which performs the calculation by using all elements in the submatrix.

The preferred embodiments of the present invention are now illustrated with reference to the appended drawings.

Embodiment 1

This embodiment explains an apparatus which transmits and receives ultrasound waves, performs delay processing on the received signals, and thereafter performs adaptive signal processing.

Figure 7:
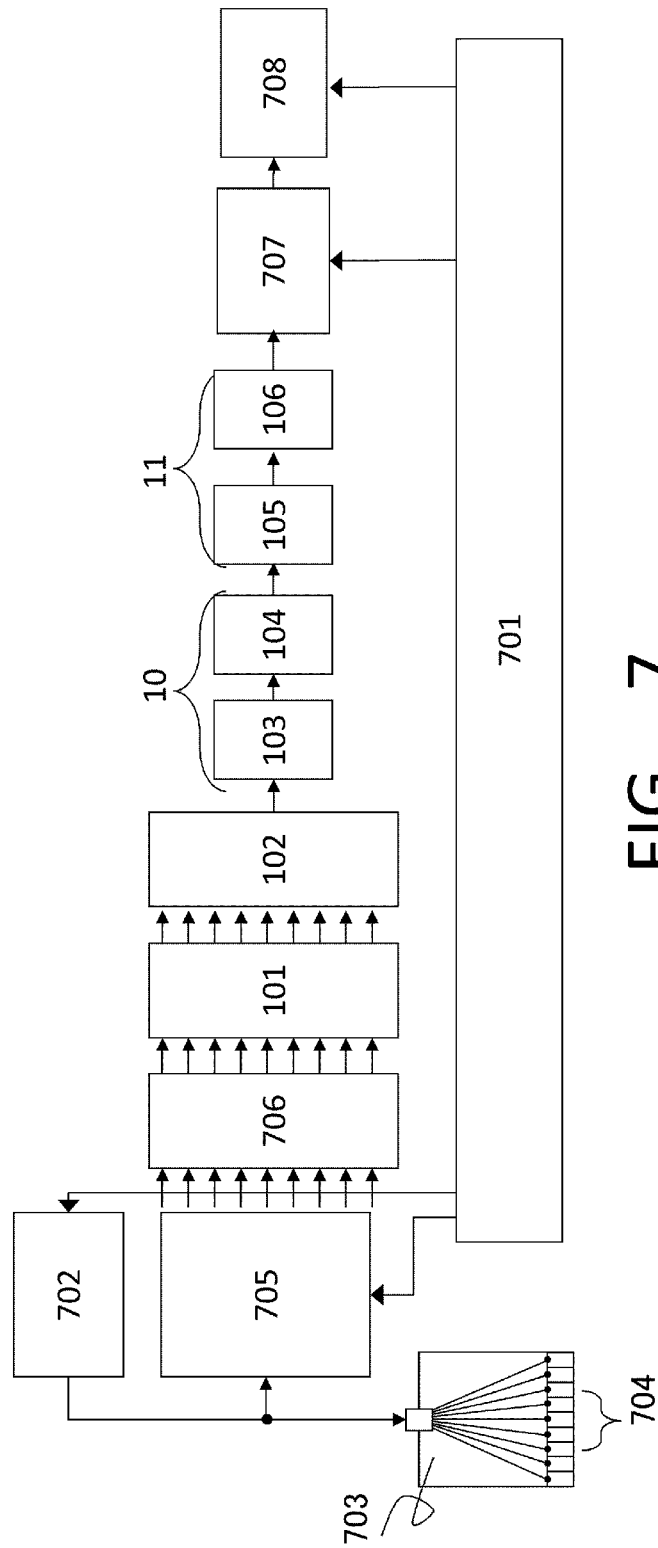
FIG. 7 is a schematic diagram of the system of the ultrasound imaging apparatus according to the first embodiment.

FIG. 7 is a schematic diagram of the system of the ultrasound imaging apparatus according to this embodiment.

The ultrasound wave transmitting operation is foremost explained.

Information according to the transmitting direction is input from the system controller 701 to the transmitting circuit 702. The transmitting circuit 702 calculates the delay time according to the sequence of the plurality of conversion elements 704 of the probe 703, and outputs the voltage waveform (transmitted signals). This voltage waveform is converted into ultrasound waves by the plurality of conversion elements 704, and the ultrasound waves are transmitted into the object.

The receiving operation is now explained.

The ultrasound waves that were reflected according to the acoustic impedance distribution in the object are converted into electrical signals (received signals) by the conversion elements 704, and input to the receiving circuit 705. The receiving circuit 705 amplifies the electrical signals based on the gain designated from the system controller 701. The receiving circuit 705 additionally converts the electrical signal into digital data with the AD conversion circuit.

The delay processing circuit 706 performs delay processing, or phasing processing, so that the phases of the received signals from the target position will match by using the input digital data and the target position information input from the system control system 701. When ultrasound waves are transmitted, the target position is moved along the transmitting direction thereof. The delay processing circuit corresponds to the delay processor of the present invention.

As a result of using the signals that were subject to delay processing as described above, adaptive signal processing can be stably performed even to received signals of a wide band of 70% or more in a fractional bandwidth that is used in a general ultrasound device, and the spatial resolution can be improved further.

The plurality of digital data that was subject to delay processing are subject to the Hilbert transformation by the Hilbert transformation circuit 101. Among the plurality of digital signals that were transformed into a complex representation by the correlation Hilbert transformation, data is clipped only for the time required for the averaging in order to calculate the correlation data.

The correlation calculation circuit 102 calculates the correlation data by using the clipped data.

Here, assuming a case where 32 elements worth of signals are input, the processing in the case of using the correlation calculation circuit to calculate the correlation data of input signals that are separated by two input signals is now explained with reference to FIG. 8.

Figure 8:
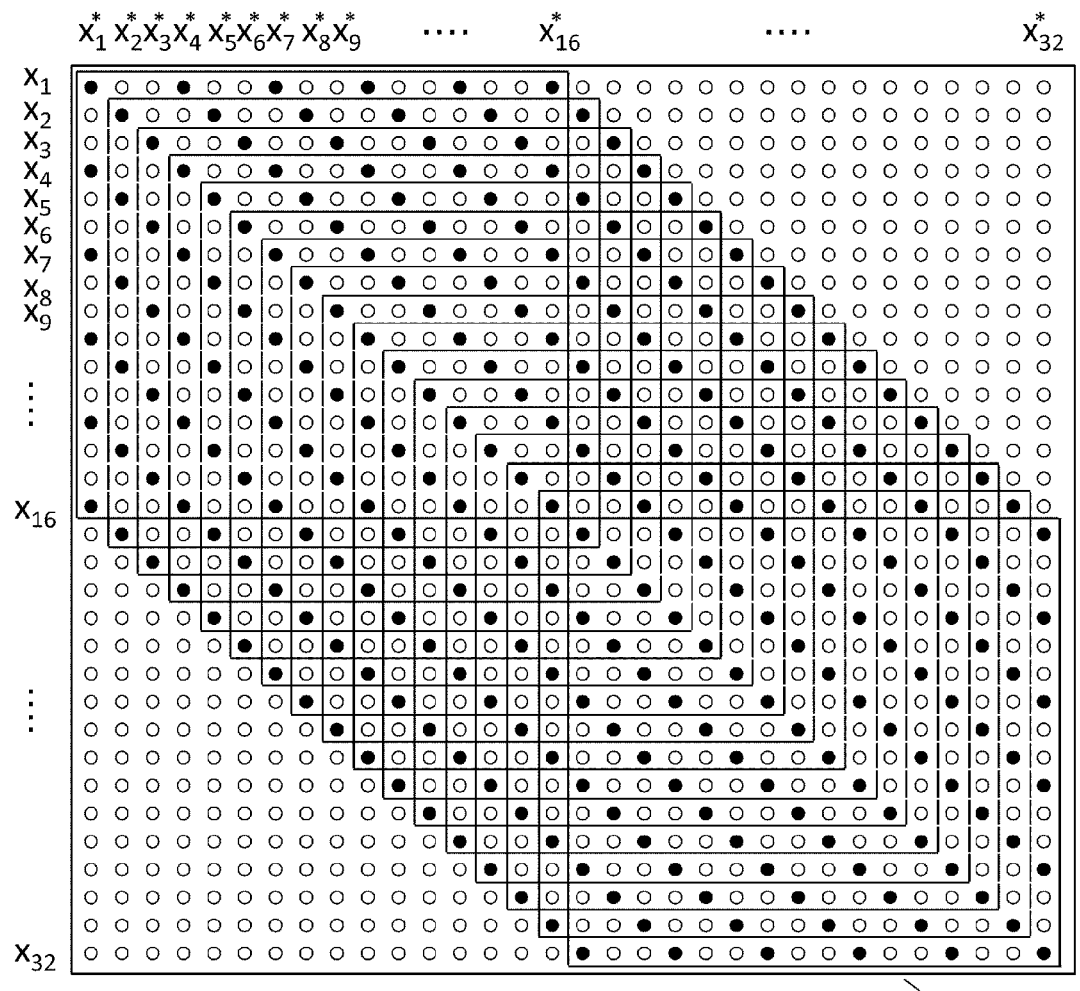
FIG. 8 is a diagram indicating the correlation matrix according to the first embodiment.

The correlation matrix 801 of FIG. 8 represents the correlation of the signals (x1 to x32, x*1 to x*32) indicated vertically and horizontally. While the 32 by 32 correlation matrix 801 can be created by using 32 elements worth of signals, the correlation calculation circuit of this embodiment performs the operation processing only to the elements of the positions indicated in black in the diagram. The positions of these elements to be subject to the operation processing are the positions of the diagonal components of the correlation matrix 801, and the positions separated at intervals of two columns from the position of the diagonal components. The contents of the operation processing are the multiplication and averaging of the input data. Here, the diagonal elements represent the self-correlation of the input signals. Moreover, the elements of combinations such as x1 and x*4, and x2 and x*5 of positions that are separated by two columns from the position of the diagonal components represent the correlation of input signals that are separated by two input signals. Multiplication is repeatedly performed in the amount of the clipped data at the position of the elements subject to operation processing, and ultimately the foregoing data is averaged and output as the correlation data. In this embodiment, the black elements; that is, the 262 elements are output as the correlation data. Note that, since the correlation matrix is a Hermitian matrix, in reality it is also possible to output only the 147 elements of the diagonal elements and the elements of the upper or lower triangular matrix.

The average circuit 10 uses the calculated correlation data as the input, and outputs the average correlation matrix based on the element extraction circuit 103 which extracts the elements to be used in the average correlation matrix, and the element average circuit 104 which averages these element and calculates the average correlation matrix.

Figure 9:
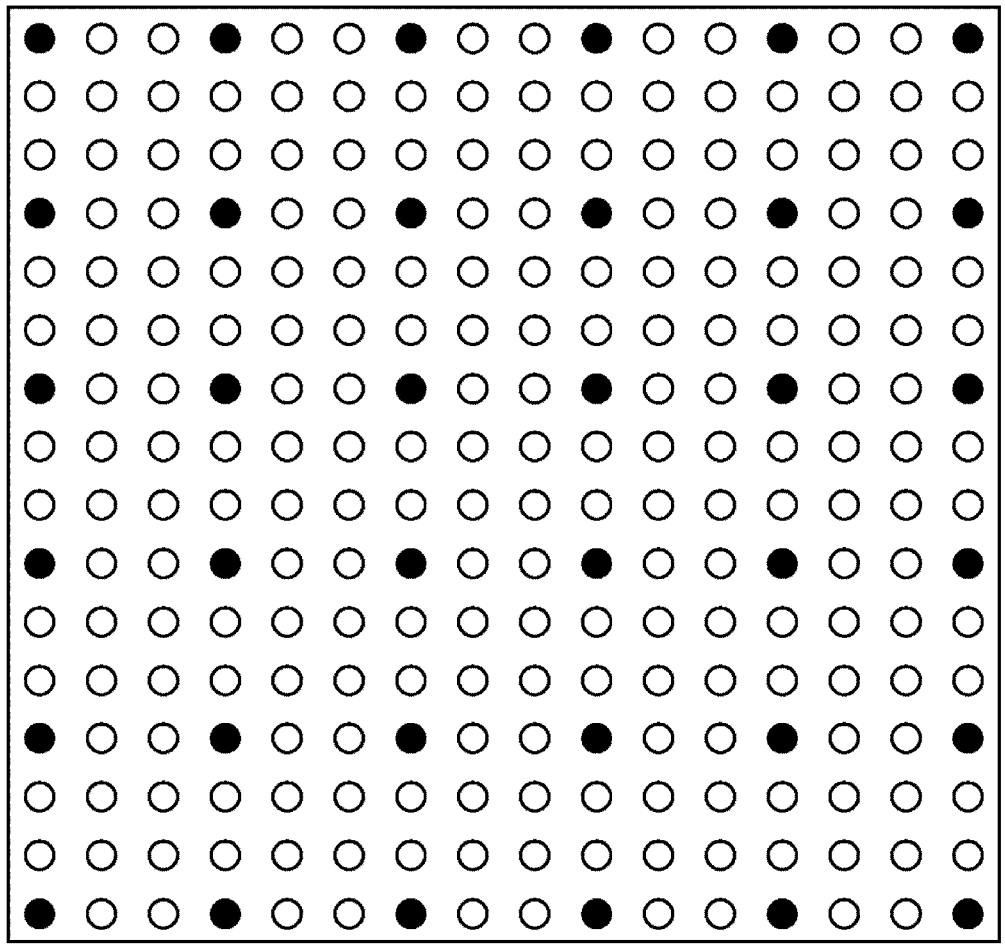
FIG. 9 is a diagram showing the average correlation matrix according to the first embodiment.

FIG. 9 is a diagram explaining the concept of the average correlation matrix in this embodiment. The size of the submatrix that is extracted in the correlation matrix 801 is 16 by 16, but when actually calculating the average correlation matrix, the average correlation matrix is calculated by using the elements at the positions shown with black circles in FIG. 9 within the submatrix. In other words, the correlation of signals separated by two signals among the input signals is used in the respective submatrices. Ultimately, the size of the average correlation matrix that is output from the average circuit 10 will be 6 by 6.

In comparison to the fact that the size of the spatial average correlation matrix that is calculated by directly using the spatial averaging method without applying the present invention will be 16 by 16, the processing volume that is required for the inverse matrix operation is suppressed to approximately 1/20 (approximately equals to $(6/16)^3$). Note that, although the input of 32 elements was used in the foregoing explanation, the effect of the present invention can be yielded regardless of the number of input signals.

Subsequently, the adaptive processing circuit 11 inputs the average correlation matrix, implements the adaptive signal processing with the inverse matrix operation circuit 105 which calculates the inverse matrix and the power calculation circuit 106 which calculates the power using the calculated inverse matrix, and then outputs the power. Note that, in this embodiment, the delay processing is performed in advance, the vector of 1 is used as the steering vector in all cases.

This kind of processing is continuously performed while moving the target position in the transmitting direction, and similar processing is further repeated by changing the transmitting direction. Consequently, internal information of the object can be generated and acquired as the power distribution showing the power of each target position.

The display processing system 707 performs log compression and image processing (edge enhancement, smoothing and the like) based on various image filters or the like with the power distribution showing the power of each target position in the object as the input. In addition, the display processing system 707 additionally performs processing corresponding to the display method designated by the system controller 701, and outputs the image data to the image display device 708 so as to display the image.

Figure 10A:
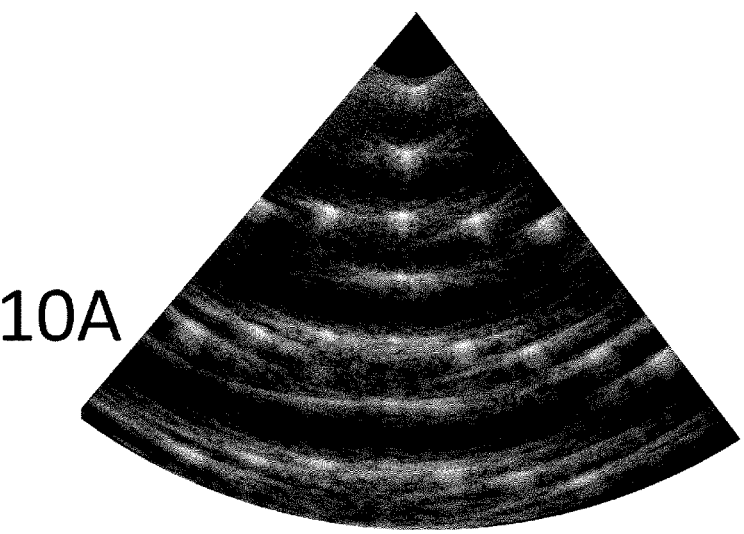
FIGS. 10A to 10C are diagrams showing the processing results according to the first embodiment.
Figure 10B:
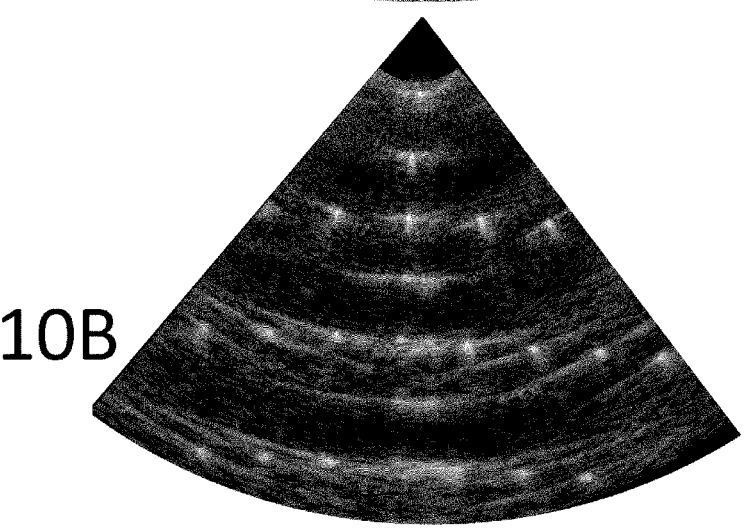
Figure 10C:
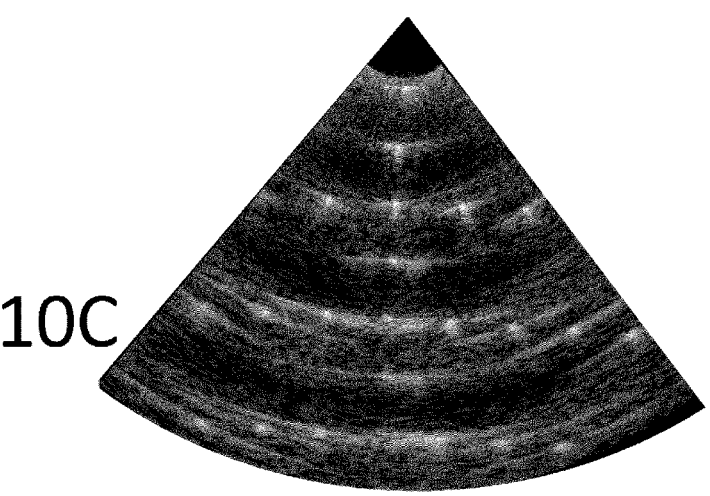

FIG. 10 shows the results of performing sector scanning to the wire phantom based on this embodiment, and processing the received signals. FIG. 10A shows the results upon performing so-called delay-and-sum without performing adaptive signal processing. FIG. 10B shows the results of performing adaptive signal processing by using the correlation data of signals that are separated by one signal in the processing method illustrated in this embodiment. FIG. 10C shows the results of performing adaptive signal processing by using the correlation data of signals that are separated by two signals. Since the adaptive signal processing is performed by using the correlation data of signals that are separated by one signal or signals that are separated by two signals, the processing volume required for the inverse matrix operation is reduced. Moreover, in comparison to FIG. 10A, with the images of FIG. 10B and FIG. 10C, it is evident that the resolution in the orientation direction (central angle direction) of the sector scanning is improved.

Accordingly, with this embodiment, it is possible to realize an apparatus having a high spatial resolution while reducing the volume of adaptive signal processing.

In this embodiment, although the present invention was applied to the reflected signals resulting from the transmission of ultrasound waves, similar processing can also be performed to ultrasound waves (photoacoustic waves) that are generated by optical irradiation using the photoacoustic effect, and similar effects can also be obtained. In other words, by providing a light source as a part of the device configuration, the processing of the present invention can be performed to the photoacoustic waves emitted from an object that absorbed electromagnetic waves (light) irradiated from the light source.

While the Hilbert transformation was performed to the signals that were subject to delay processing in this embodiment, the effects of the present invention can also be obtained by performing delay processing on the signals that were subject to the Hilbert transformation.

Embodiment 2

This embodiment explains an ultrasound imaging apparatus that uses moving average signals obtained based on the moving average among the input signals. In particular, the differences in comparison to the foregoing embodiment are mainly explained.

Figure 11:
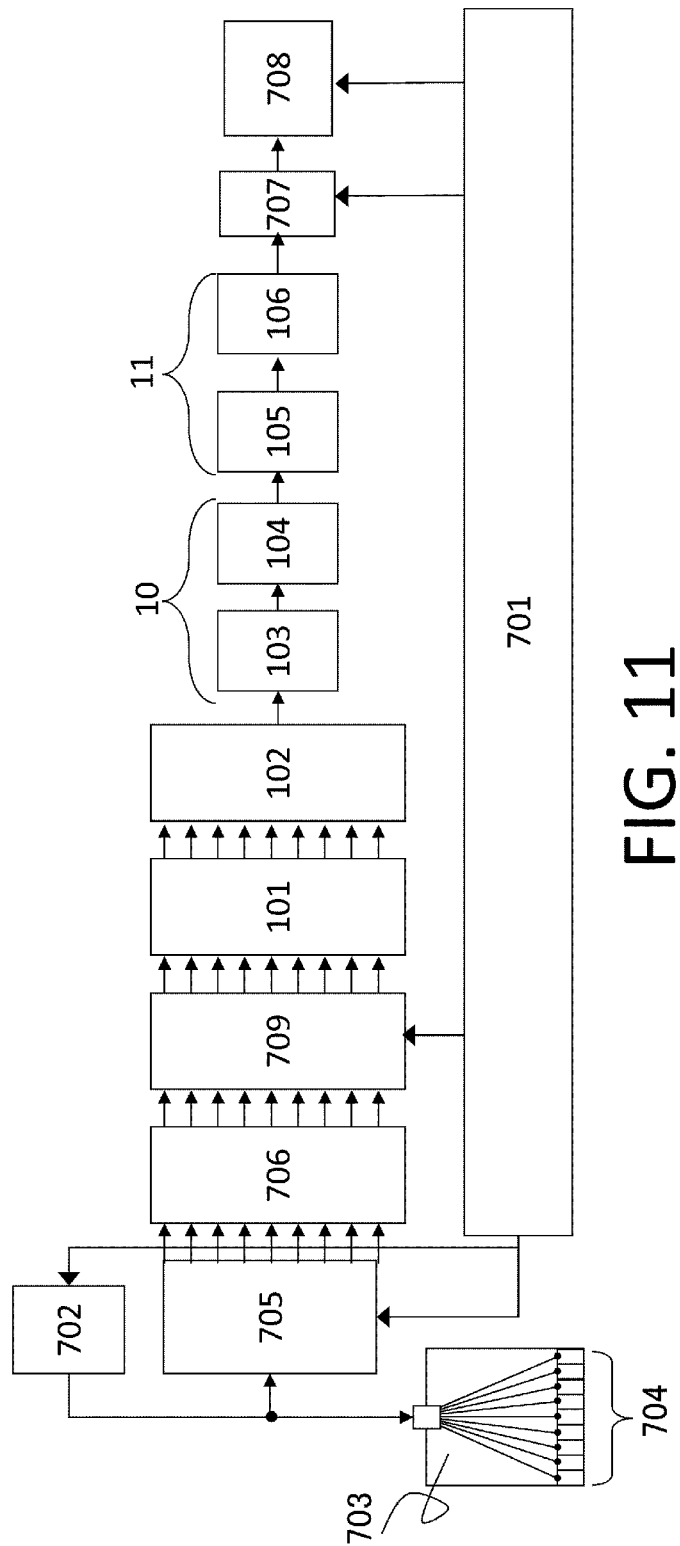
FIG. 11 is a schematic diagram of the system of the ultrasound imaging apparatus according to the second embodiment.

FIG. 11 is a schematic diagram of the system of the ultrasound imaging apparatus according to this embodiment. It is evident that a moving average circuit 709 is provided by referring to the diagram. The moving average circuit corresponds to the moving average processor of the present invention.

In this embodiment also, the transmission of ultrasound waves is performed as with the foregoing embodiment. The receiving operation of this embodiment is now explained. The ultrasound waves that were reflected according to the acoustic impedance distribution in the object are converted into electrical signals by the conversion element 704, and thereafter input to the receiving circuit 705. The receiving circuit 705 amplifies the electrical signals based on the gain designated from the system controller 701 and converts the electrical signals into digital data with the AD conversion circuit.

The delay processing circuit 706 performs delay processing, or phasing processing, so that the phases of the received signals from the target position will match by using the input digital data and the target position information input from the system control system 701. When ultrasound waves are transmitted, the target position is moved along the transmitting direction thereof.

The plurality of digital data that was subject to delay processing are input to the moving average circuit 709. The moving average circuit 709 obtains the moving average among the input signals by using the aperture size designated by the system controller 701. For example, the aperture size of the moving average is 2, and the input signals are represented as follows.

$x_1, x_2, x_3, \ldots, x_N$

Consequently, the moving average signals $y_1, y_2, \ldots, y_{N-1}$ are calculated as follows.

$y_1=(x_1+x_2)/2, y_2=(x_2+x_3)/2, \ldots, y_{N-1}=(x_{N-1}+x_N)/2$

Generally speaking, when the aperture size of the moving average is A, Nch worth of input signals are $x_k$ (k=1, 2, ..., N), and the moving average signals are $y_k$ (k=1, 2, ..., N−A+1), this can be represented as shown in Formula (12). Note that, if the aperture size is A, it goes without saying that A is an integer of 2 or higher in light of obtaining the average.

[Math. 10]

$$y_k = \sum_{m=k}^{k+A-1} \frac{1}{A} x_m \qquad (12)$$

The moving average signals Y ($y_1, y_2, \ldots, y_{N-A+1}$) are subject to the Hilbert transformation by the Hilbert transformation circuit 101. Among the plurality of digital signals that were converted into a complex representation by the Hilbert transformation, data is clipped only for the time required for the averaging in order to calculate the correlation data The correlation calculation circuit 102 to which the clipped data is input calculates the correlation of signals separated by one or more signals, and outputs the result as correlation data.

As a result of using the signals that were subject to moving average as the input signals of the correlation calculation circuit, it is possible to calculate the correlation data using input signals in which the SN ratio is of a high state, and it is thereby possible to obtain images with an even higher SN ratio.

Figure 12:
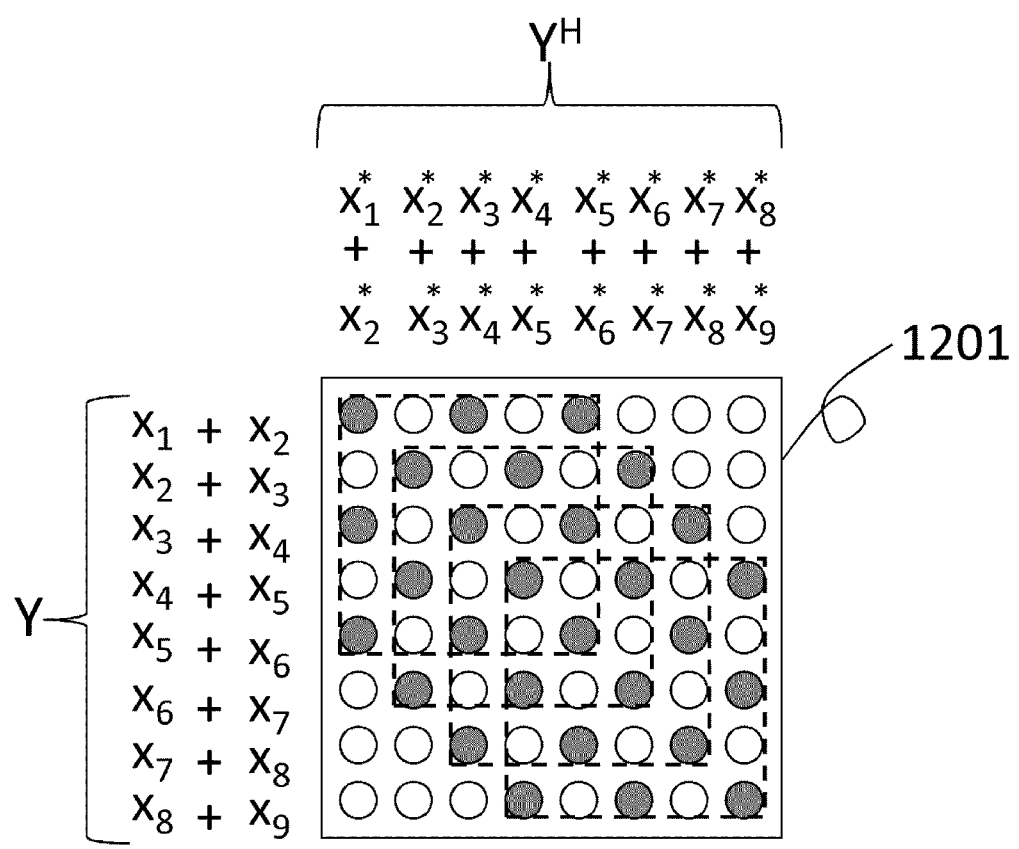
FIG. 12 is a diagram explaining the calculation method of correlation data according to the second embodiment.
Figure 13A:
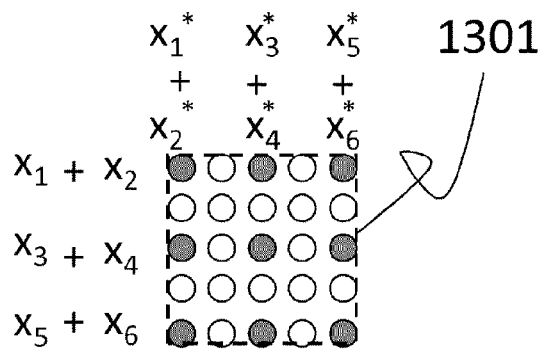
FIGS. 13A to 13D are diagrams showing the average correlation matrix according to the second embodiment.
Figure 13B:
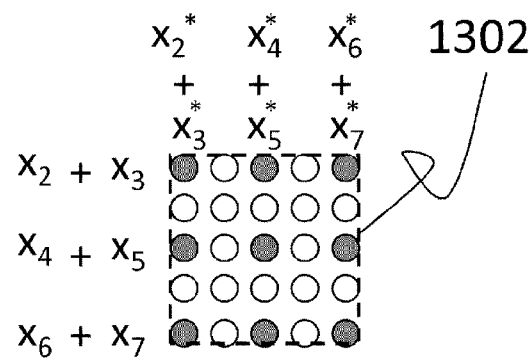
Figure 13C:
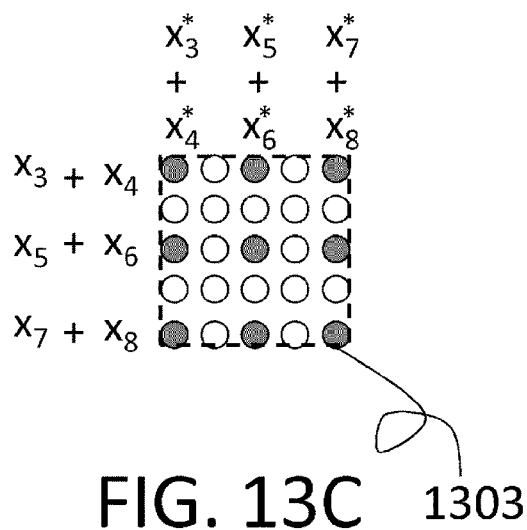
Figure 13D:
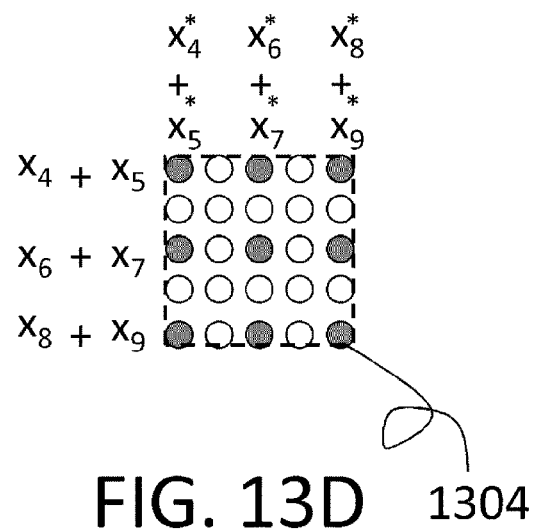

The processing of using 9 elements worth of received signals and calculating the correlation of the signals separated by one signal in the case where the aperture size of the moving average is 2 is now explained with reference to FIG. 12. The moving average circuit to which 9 elements worth of received signals was input performs the moving average processing with an aperture size of the moving average of 2, and outputs eight types of moving average signals Y ($y_1, y_2, \ldots, y_8$). The 8 by 8 correlation matrix 1201 can be created by using the foregoing moving average signals Y. The correlation calculation circuit of this embodiment performs multiplication of the elements at the colored positions in the diagram, and outputs the result as the correlation data.

The average circuit 10 uses the calculated correlation data as the input, and outputs the average correlation matrix based on the element extraction circuit 103 which extracts the elements to be used in the average correlation matrix, and the element average circuit 104 which averages these element and calculates the average correlation matrix.

FIG. 13 is a diagram explaining the concept of the average correlation matrix in this embodiment. FIGS. 13A to 13D respectively correspond to the submatrices 1301 to 1304. The size of the submatrix that is extracted in the correlation matrix 1201 is 5 by 5. When actually calculating the average correlation matrix, the average correlation matrix is calculated by using the elements at the colored positions in the respective submatrices 1301 to 1304. In other words, the correlation of signals separated by one signal among the input signals is used in the respective submatrices. In the foregoing case, the size of the average correlation matrix that is output from the average circuit 10 will be 3 by 3.

Meanwhile, the size of the spatial average correlation matrix that is calculated by directly using the spatial averaging method without applying the present invention will be 5 by 5. Accordingly, when the present invention is applied, the processing volume that is required for the inverse matrix operation is suppressed to approximately 1/4.6 (approximately equals to $(3/5)^3$). Note that, although the input of 9 elements was used in the foregoing explanation, the effect of the present invention can be yielded regardless of the number of input signals.

Here, upon focusing on the submatrix 1301, the data for which the correlation is to be obtained will be ($x_1+x_2$), ($x_3+x_4$), ($x_5+x_6$), and this is an input from mutually continuous elements. When the aperture size of the moving average is set to A, the correlation data calculated among the respective submatrices will be an input from mutually continuous elements by calculating the correlation data of signals that are separated by (A−1) signals in the correlation calculation circuit. As a result of using the input from continuous elements as described above, it is possible to suppress the generation of side lobes and grating lobes, and obtain images having even a higher SN ratio.

Note that, even when the relation of the aperture size of the moving average and the number of signals that used as the separating interval upon calculating the correlation data with the correlation calculation circuit is other than as described above, it is still possible to obtain the effects of the present invention; namely, reduction of the processing volume and improvement of the spatial resolution.

The subsequent processing of the adaptive processing circuit 11 is the same as the foregoing embodiments, and the explanation thereof is omitted.

Figure 14A:
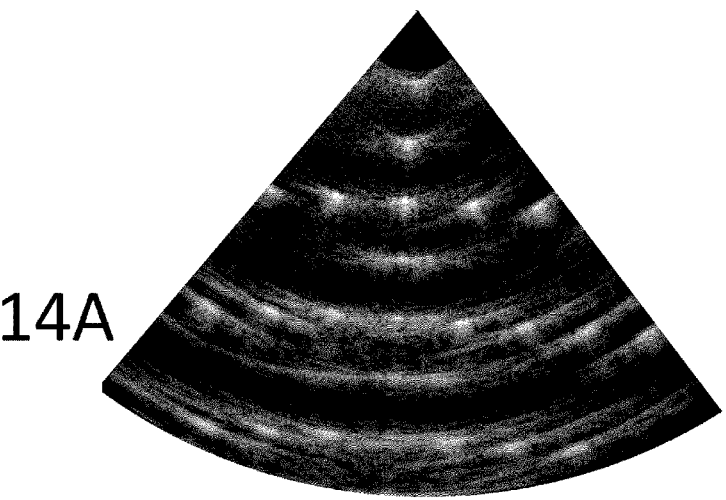
FIGS. 14A to 14C are diagrams showing the processing results according to the second embodiment.
Figure 14B:
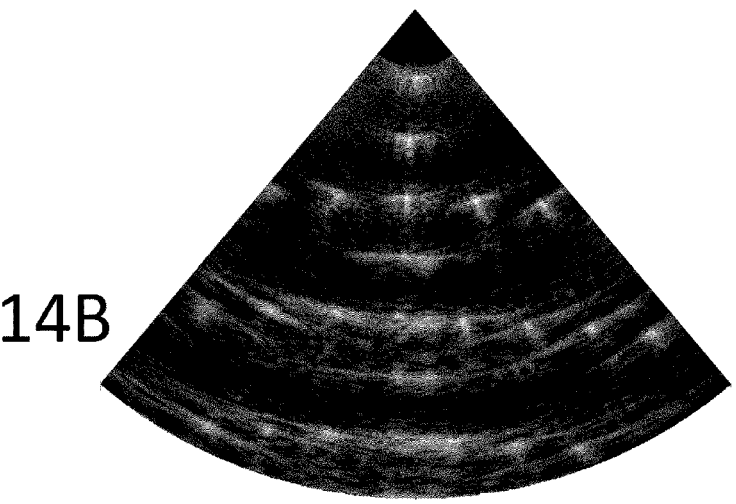
Figure 14C:
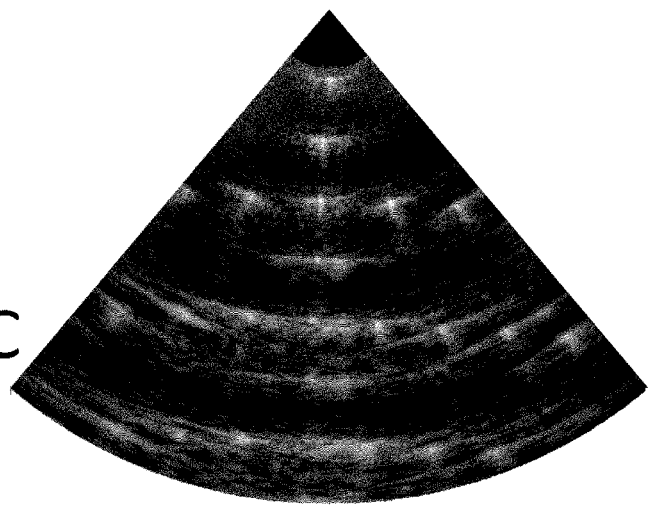

FIG. 14 shows the results of performing sector scanning and processing the received signals in this embodiment. FIG. 14A shows the results upon performing so-called delay-and-sum without performing adaptive signal processing. FIG. 14B shows the results of performing adaptive signal processing by using the correlation data of signals that are separated by one signal and in which the aperture size of the moving average is 2 in the processing method illustrated in this embodiment. FIG. 14C shows the results of performing adaptive signal processing by using the correlation data of signals that are separated by two signals and in which the aperture size of the moving average is 3.

In comparison to the processing of FIG. 14A, since the processing of FIGS. 14B and 14C performs adaptive signal processing by using the correlation data of signals that are separated by one signal or signals that are separated by two signals, the processing volume required for the inverse matrix operation is reduced. Moreover, with the images of FIG. 14B and FIG. 14C, it is evident that the resolution in the orientation direction of the sector scanning is improved. In addition, it is also evident that the SN ratio of the image has improved in comparison to the foregoing embodiment.

Accordingly, with this embodiment, the adaptive signal processing can be performed in a state where the SN ratio of signals is higher by performing the moving average processing. Consequently, it is possible to realize an ultrasound imaging apparatus capable of suppressing the processing volume, improving the spatial resolution, and additionally obtaining images having a high SN ratio.

In this embodiment, although the present invention was applied to the reflected signals resulting from the transmission of ultrasound waves, similar processing can also be performed to ultrasound waves (photoacoustic waves) that are generated by optical irradiation using the photoacoustic effect, and similar effects can also be obtained.

In this embodiment, the signals subject to delay processing were subject to moving average processing and additionally subject to the Hilbert transformation, but the moving average processing and the Hilbert transformation are interchangeable, and the same results can be obtained even when the order of processing is switched.

Embodiment 3

This embodiment explains an ultrasound imaging apparatus including a signal addition circuit which adds and outputs delay signals. In particular, the differences in comparison to the foregoing embodiments are mainly explained.

Figure 15:
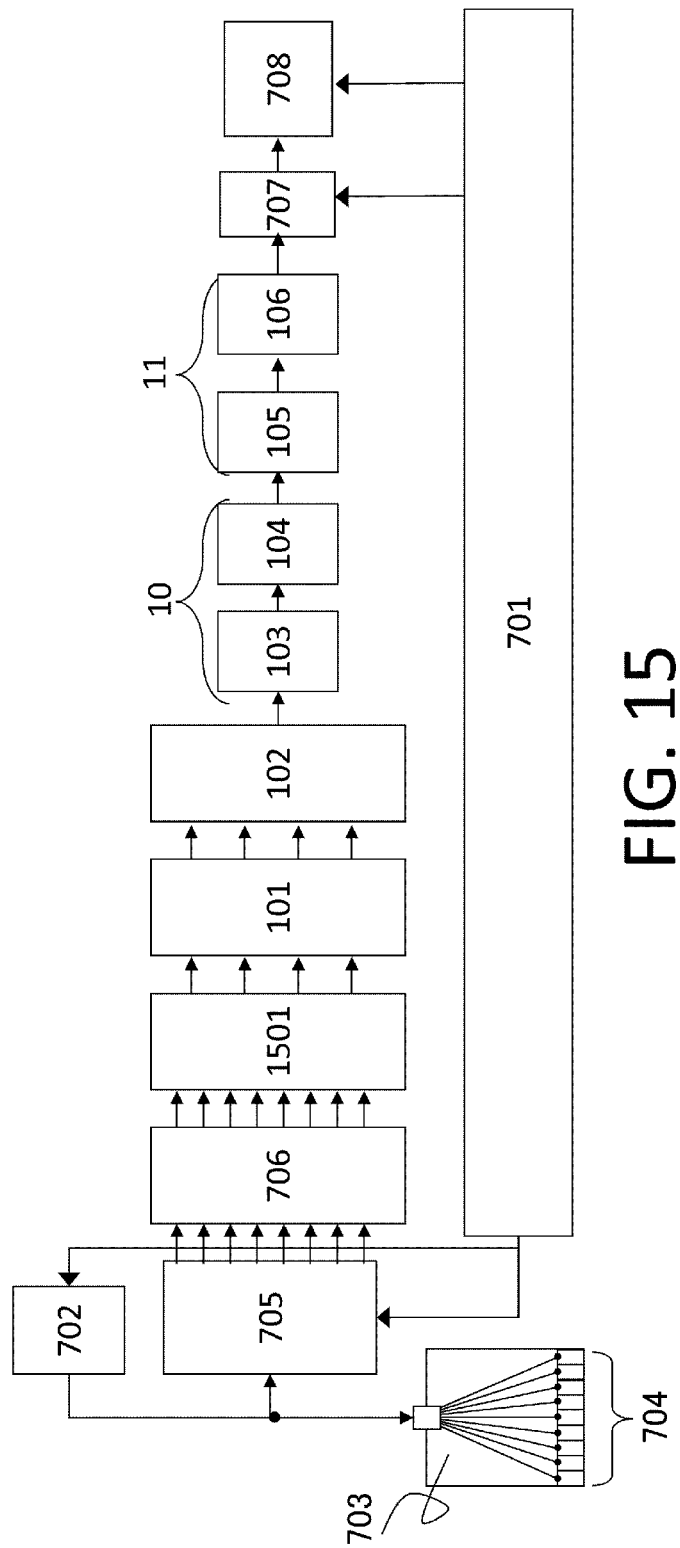
FIG. 15 is a schematic diagram of the system of the ultrasound imaging apparatus according to the third embodiment.

FIG. 15 is a schematic diagram of the system of the ultrasound imaging apparatus according to this embodiment. It is evident that a signal addition circuit 1501 is provided in substitute for the moving average circuit 709 in comparison to Embodiment 2. The signal addition circuit corresponds to the signal adder of the present invention.

In this embodiment also, the transmission of ultrasound waves is performed as with the foregoing embodiments.

The receiving operation of this embodiment is now explained. The ultrasound waves that were reflected according to the acoustic impedance distribution in the object are converted into electrical signals by the conversion element 704, and thereafter input to the receiving circuit 705. The receiving circuit 705 amplifies the electrical signals based on the gain designated from the system controller 701 and converts the electrical signals into digital data with the AD conversion circuit.

The delay processing circuit 706 performs delay processing, or phasing processing, so that the phases of the received signals from the target position will match by using the input digital data and the target position information input from the system control system 701. When ultrasound waves are transmitted, the target position is moved along the transmitting direction thereof.

The plurality of digital data that was subject to delay processing are input to the signal addition circuit 1501. The signal addition circuit 1501 performs the addition processing of the input signals and outputs the plurality of signals that were subject to addition processing. For example, the addend is 2, and the input signals are represented as follows.

$x_1, x_2, x_3, \ldots, x_N$ (wherein N is a multiple of 2)

Consequently, the signals $y_2, y_2, \ldots, Y_{N/2}$ that were subject to addition processing are calculated as follows.

$$y_1 = x_1 + x_2, y_2 = x_3 + x_4, \ldots, y_{N/2} = x_{N-1} + x_N$$

Generally speaking, when the average number of signals is B, Nch worth of input signals are $x_k$ (k=1, 2, ..., N), and the moving average signals are $y_k$ (k=1, 2, ..., floor[N/B]), this can be represented as shown in Formula (13).

[Math. 11]

$$y_k = \sum_{m=B \times (k-1)+1}^{B \times k} x_m \quad (13)$$

However, floor [ ] represents the floor function, and only the integer portion is extracted.

Since this kind of signal addition circuit 1501 performs addition processing, the number of signals that are output is fewer than the number of signals that are input.

The signals Y ($y_2, y_2, \ldots, Y_{[N/B]}$) that were subject to addition processing are subject to the Hilbert transformation by the Hilbert transformation circuit 101. Among the plurality of digital signals that were converted into a complex representation by the Hilbert transformation, data is clipped only for the time required for the averaging in order to calculate the correlation data.

The correlation calculation circuit 102 to which the clipped data is input calculates the correlation of signals separated by one or more signals, and outputs the result as correlation data.

As a result of performing this kind of addition processing, the number of calculations of correlation data and the matrix size for performing the subsequent inverse matrix operation can be further reduced, and the processing volume can be further suppressed.

Figure 16:
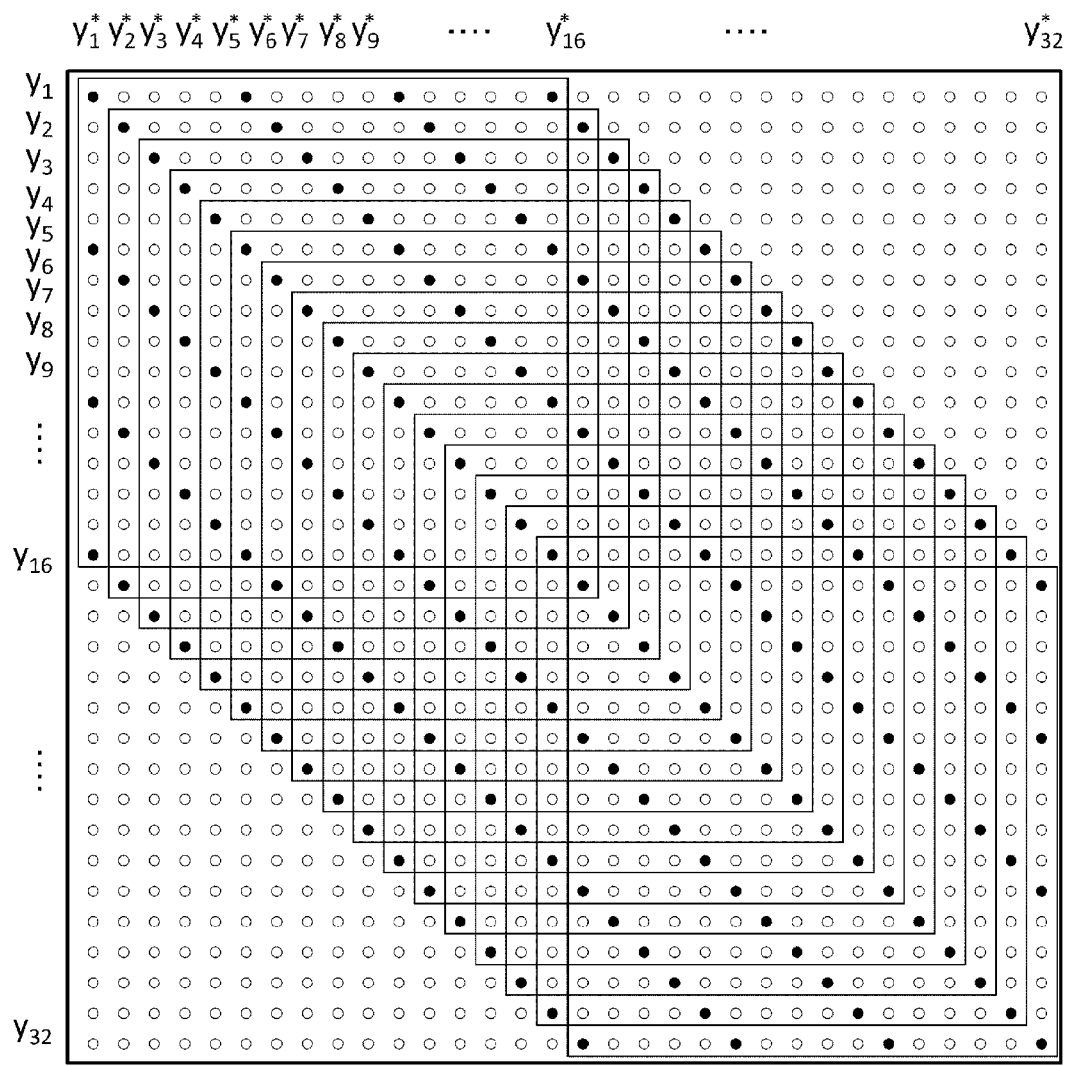
FIG. 16 is a diagram indicating the correlation matrix according to the third embodiment.

The processing of using 96 elements worth of received signals and calculating the correlation of the signals separated by four signals in the case where the addend of the addition processing is 3 is now explained with reference to FIG. 16. The addition processing circuit to which 96 elements worth of received signals was input performs the addition processing with an addend of 3, and outputs 32 types of signals Y ($y_1, y_2, \ldots, y_{32}$) that were subject to the addition processing.

The 32 by 32 correlation matrix 1601 can be created by using the signals Y that were subject to the foregoing addition processing as the input signals of the correlation calculation circuit. The correlation calculation circuit of this embodiment performs multiplication of the elements at the positions shown with black circles in FIG. 16, and outputs the result as the correlation data. The positions of these elements that are subject to multiplication are the positions of the diagonal components of the correlation matrix 1601, and the positions that are separated by four columns from the positions of the diagonal components. These positions represent the correlation of the signals that are separated by four signals among the input signals. This kind of operation is repeatedly performed in the amount of the clipped data.

The average circuit 10 uses the calculated correlation data as the input, and outputs the average correlation matrix based on the element extraction circuit 103 which extracts the elements to be used in the average correlation matrix, and the element average circuit 104 which averages these element and calculates the average correlation matrix.

Figure 17:
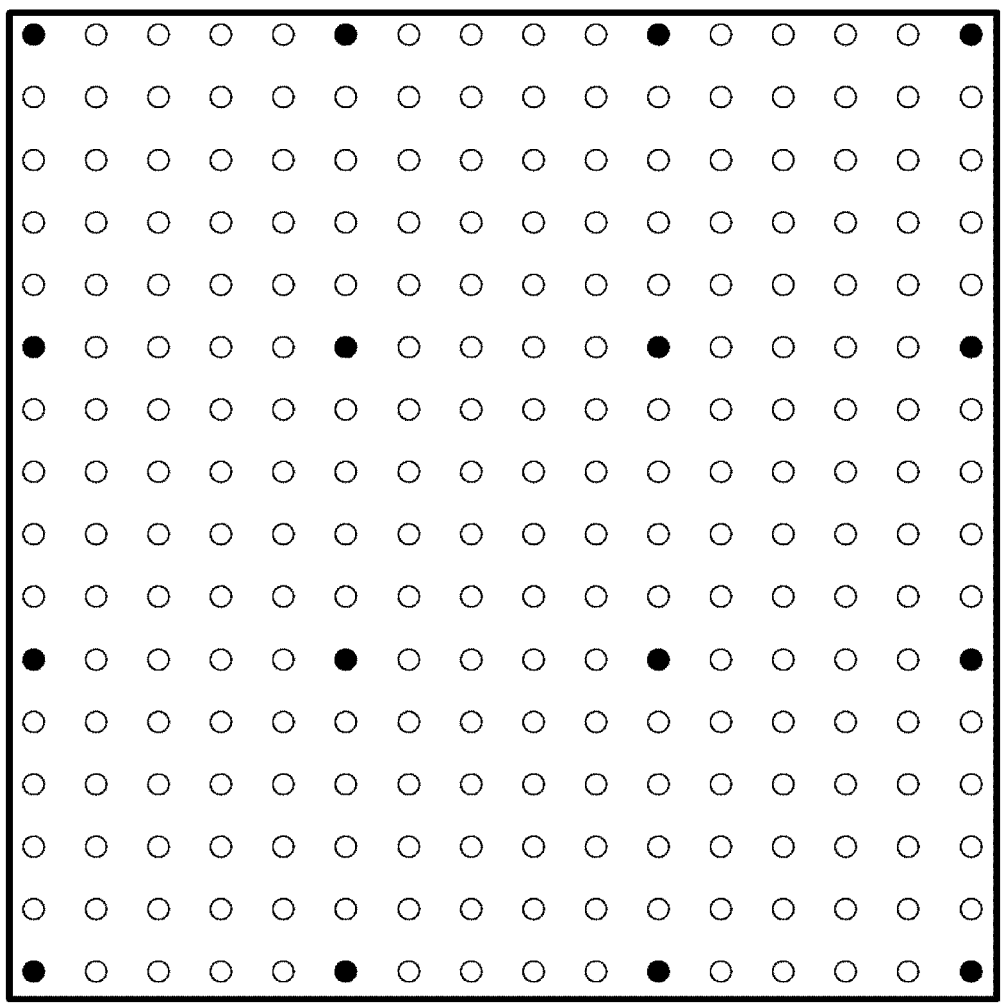
FIG. 17 is a diagram showing the average correlation matrix according to the third embodiment.

FIG. 17 is a diagram explaining the concept of the average correlation matrix in this embodiment. The size of the submatrix that is extracted in the correlation matrix 1601 is 16 by 16, but when actually calculating the average correlation matrix, the average correlation matrix is calculated by using the elements at the positions shown with black circles in FIG. 17 within the submatrix. In other words, the correlation of signals separated by four signals among the input signals is used in the respective submatrices. Specifically, the size of the average correlation matrix that is output from the average circuit 10 will be 4 by 4.

In comparison to the fact that the size of the spatial average correlation matrix that is calculated by directly using the spatial averaging method without applying the present invention will be 48 by 48, the processing volume that is required for the inverse matrix operation is suppressed to approximately 1/1700 (approximately equals to $(4/48)^3$).

The subsequent processing of the adaptive processing circuit 11 is the same as the foregoing embodiments, and the explanation thereof is omitted.

Accordingly, with this embodiment, it is possible to realize an ultrasound imaging apparatus capable of further suppressing the processing volume by performing the addition processing, and obtaining images with an improved spatial resolution.

In this embodiment, although the present invention was applied to the reflected signals resulting from the transmission of ultrasound waves, similar processing can also be performed to ultrasound waves (photoacoustic waves) that are generated by optical irradiation using the photoacoustic effect, and similar effects can also be obtained.

Moreover, by installing the moving average circuit explained in Embodiment 2 between the signal addition circuit 1501 and the Hilbert transformation circuit 101, it is possible to realize an ultrasound imaging apparatus capable of providing images with even a higher SN ratio.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-105318, filed on May 10, 2011, which is hereby incorporated by reference herein in its entirety.

The invention claimed is:

1. An object information acquiring apparatus, comprising:
a plurality of conversion elements which receive acoustic waves emitted from an object and convert the acoustic waves into electrical signals;
a correlation calculator which calculates correlation data by using the plurality of electrical signals output from said plurality of conversion elements;
an average correlation calculator which calculates an average correlation matrix by extracting a plurality of submatrices from the correlation data and averaging the submatrices; and
an adaptive signal processor which generates power distribution by performing adaptive signal processing by using the average correlation matrix and calculating the power of each target position,
wherein said correlation calculator calculates the correlation data by obtaining the correlation of input signals that are separated by at least one input signal among the input signals input to said correlation calculator and without obtaining the correlation of input signals that are not separated by at least one input signal among the input signals input to said correlation calculator, and
wherein the correlation data calculated with said correlation calculator contains only elements of diagonal components of the correlation matrix, and elements at positions that are separated at intervals of one or more columns from the elements of the diagonal components.

2. The object information acquiring apparatus according to claim 1, wherein said adaptive signal processor obtains the power by obtaining an inverse matrix of the average correlation matrix, or performing QR decomposition and back substitution processing on the average correlation matrix.

3. The object information acquiring apparatus according to claim 1, wherein said average correlation calculator performs averaging only on elements contained in the plurality of submatrices, among the elements of the correlation data.

4. The object information acquiring apparatus according to claim 1, further comprising:
a delay processor which performs delay processing on the plurality of electrical signals according to a target position in the object,
wherein said correlation calculator calculates the correlation matrix with the electrical signals output from said delay processor as the input signals.

5. The object information acquiring apparatus according to claim 1, further comprising:
a moving average processor which performs moving average processing on the plurality of electrical signals and calculates moving average signals,
wherein said correlation calculator calculates the correlation matrix with the moving average signals as the input signals.

6. The object information acquiring apparatus according to claim 4, further comprising:
a moving average processor which performs moving average processing on the electrical signals output from said delay processor and calculates moving average signals,
wherein said correlation calculator calculates the correlation matrix with the moving average signals as the input signals.

7. The object information acquiring apparatus according to claim 5, wherein, if an aperture size when said moving average processor performs the moving average processing is A (wherein A is an integer equal to or greater than 2), said correlation calculator obtains the correlation of the input signals that are separated by (A−1) input signals.

8. The object information acquiring apparatus according to claim 1, further comprising:
a signal adder which performs addition processing on the plurality of electrical signals, wherein said correlation calculator calculates the correlation matrix with the electrical signals output from said signal adder as the input signals.

9. The object information acquiring apparatus according to claim 4, further comprising:
a signal adder which performs addition processing on the electrical signals output from said delay processor,
wherein said correlation calculator calculates the correlation matrix with the electrical signals output from said signal adder as the input signals.

10. The object information acquiring apparatus according to claim 1, wherein the acoustic waves emitted from the object result from the acoustic waves output from said conversion elements being reflected inside the object.

11. The object information acquiring apparatus according to claim 1, further comprising:
a light source which irradiates the object with electromagnetic waves,
wherein the acoustic waves emitted from the object are photoacoustic waves emitted from the object irradiated with the electromagnetic waves.

12. An object information acquiring method, comprising:
a correlation calculation step of calculating correlation data by using a plurality of electrical signals output from a plurality of conversion elements which receive acoustic waves emitted from an object;

an average correlation calculation step of calculating an average correlation matrix by extracting a plurality of submatrices from the correlation data and averaging the submatrices; and an adaptive signal processing step of generating power distribution by performing adaptive signal processing by using the average correlation matrix and calculating the power of each target position, wherein, in said correlation calculation step, the correlation data is calculated by obtaining the correlation of input signals that are separated by at least one input signal among the input signals input in said correlation calculation step and without obtaining the correlation of input signals that are not separated by at least one input signal among the input signals input in said correlation calculation step, and wherein the correlation data calculated in said correlation calculation step contains only elements of diagonal components of the correlation matrix, and elements at positions that are separated at intervals of one or more columns from the elements of the diagonal components.

13. The object information acquiring method according to claim 12, wherein, in said adaptive signal processing step, the power is obtained by obtaining an inverse matrix of the average correlation matrix, or performing QR decomposition and back substitution processing on the average correlation matrix.

14. The object information acquiring method according to claim 12, wherein, in said average correlation calculation step, averaging is performed only on elements contained in the plurality of submatrices, among the elements of the correlation data.

15. The object information acquiring method according to claim 12, further comprising:
a delay processing step of performing delay processing on the plurality of electrical signals according to a target position in the object,
wherein, in said correlation calculation step, the correlation matrix is calculated with the electrical signals output in said delay processing step as the input signals.

16. The object information acquiring method according to claim 12, further comprising:
a moving average processing step of performing moving average processing on the plurality of electrical signals and calculating moving average signals,
wherein, in said correlation calculation step, the correlation matrix is calculated with the moving average signals as the input signals.

17. The object information acquiring method according to claim 15, further comprising:
a moving average processing step of performing moving average processing on the electrical signals output in said delay processing step and calculating moving average signals,
wherein, in said correlation calculation step, the correlation matrix is calculated with the moving average signals as the input signals.

18. The object information acquiring method according to claim 16, wherein, if an aperture size when the moving average processing is performed in said moving average processing step is A (wherein A is an integer equal to or greater than 2), the correlation of the input signals that are separated by (A−1) input signals is obtained in said correlation calculation step.

19. The object information acquiring method according to claim 12, further comprising:

a signal adding step of performing addition processing on the plurality of electrical signals,
wherein, in said correlation calculation step, the correlation matrix is calculated with the electrical signals output in said signal adding step as the input signals.

20. The object information acquiring method according to claim 15, further comprising:
a signal adding step of performing addition processing on the electrical signals output in said delay processing step,
wherein, in said correlation calculation step, the correlation matrix is calculated with the electrical signals output in said signal adding step as the input signals.

21. An object information acquiring apparatus, comprising:
a correlation calculator which obtains correlation data from a correlation matrix using a plurality of electrical signals output from a plurality of conversion elements which have received acoustic waves emitted from an object and converted the acoustic waves into the electrical signals;
an average correlation calculator which calculates an average correlation matrix by averaging a plurality of submatrices obtained from the correlation matrix; and
an adaptive signal processor which generates power distribution by performing adaptive signal processing by using the average correlation matrix and calculating the power of each target position,
wherein the correlation data obtained by the correlation calculator includes a reduced number of elements of the correlation matrix, and
wherein the correlation data includes diagonal elements of the correlation matrix and elements separated from the diagonal elements by at least one row or one column.

22. The object information acquiring apparatus according to claim 21, further comprising:
a delay processor which performs delay processing on the plurality of electrical signals according to a target position in the object,
wherein said correlation calculator calculates the correlation matrix with the electrical signals output from said delay processor as the input signals.

23. The object information acquiring apparatus according to claim 21, further comprising:
a moving average processor which performs moving average processing on the plurality of electrical signals and calculates moving average signals,
wherein said correlation calculator calculates the correlation matrix with the moving average signals as the input signals.

24. The object information acquiring apparatus according to claim 22, further comprising:
a moving average processor which performs moving average processing on the electrical signals output from said delay processor and calculates moving average signals,
wherein said correlation calculator calculates the correlation matrix with the moving average signals as the input signals.

25. The object information acquiring apparatus according to claim 23, wherein, if an aperture size when said moving average processor performs the moving average processing is A (where A is an integer equal to or greater than 2), said correlation calculator obtains the correlation of the input signals that are separated by (A−1) input signals.

26. The object information acquiring apparatus according to claim 21, further comprising:

a signal adder which performs addition processing on the plurality of electrical signals, wherein said correlation calculator calculates the correlation matrix with the electrical signals output from said signal adder as the input signals.

27. The object information acquiring apparatus according to claim 22, further comprising:
a signal adder which performs addition processing on the electrical signals output from said delay processor,
wherein said correlation calculator calculates the correlation matrix with the electrical signals output from said signal adder as the input signals.

28. The object information acquiring apparatus according to claim 21, wherein the acoustic waves emitted from the object result from the acoustic waves output from said conversion elements being reflected inside the object.

29. The object information acquiring apparatus according to claim 21, further comprising:
a light source which irradiates the object with electromagnetic waves,
wherein the acoustic waves emitted from the object are photoacoustic waves emitted from the object irradiated with the electromagnetic waves.

30. An object information acquiring method, comprising:
obtaining correlation data from a correlation matrix using a plurality of electrical signals output from a plurality of conversion elements which have received acoustic waves emitted from an object and converted the acoustic waves into the electrical signals;
calculating an average correlation matrix by averaging a plurality of submatrices obtained from the correlation matrix; and
generating power distribution by performing adaptive signal processing by using the average correlation matrix and calculating the power of each target position,
wherein the correlation data obtained in the obtaining includes a reduced number of elements of the correlation matrix, and
wherein the correlation data includes diagonal elements of the correlation matrix and elements separated from the diagonal elements by at least one row or one column.

31. The object information acquiring method according to claim 30, further comprising:
performing delay processing on the plurality of electrical signals according to a target position in the object,
wherein the calculating includes calculating the correlation matrix with the electrical signals output by the performing of delay processing as the input signals.

32. The object information acquiring method according to claim 30, further comprising:
performing moving average processing on the plurality of electrical signals and calculates moving average signals,
wherein the calculating includes calculating the correlation matrix with the moving average signals as the input signals.

33. The object information acquiring method according to claim 31, further comprising:
performing moving average processing on the electrical signals output from the delay processing and calculating moving average signals,
wherein the calculating includes calculating the correlation matrix with the moving average signals as the input signals.

34. The object information acquiring method according to claim 32, wherein, if an aperture size the moving average processing is performed is A (where A is an integer equal to or greater than 2), the calculating includes obtaining the correlation of the input signals that are separated by (A−1) input signals.

35. The object information acquiring method according to claim 30, further comprising:
performing addition processing on the plurality of electrical signals, wherein the calculating includes calculating the correlation matrix with the electrical signals output from the addition processing as the input signals.

36. The object information acquiring method according to claim 31, further comprising:
performing addition processing on the electrical signals from the delay processing,
wherein the calculating includes calculating the correlation matrix with the electrical signals output from the addition processing as the input signals.

37. The object information acquiring method according to claim 30, wherein the acoustic waves emitted from the object result from the acoustic waves output from the conversion elements being reflected inside the object.

38. The object information acquiring method according to claim 30, further comprising:
irradiating the object with electromagnetic waves from a light source,
wherein the acoustic waves emitted from the object are photoacoustic waves emitted from the object irradiated with the electromagnetic waves.

* * * * *